United States Patent [19]

Cohen

[11] Patent Number: 4,774,950

[45] Date of Patent: Oct. 4, 1988

[54] HEMODYNAMICALLY RESPONSIVE SYSTEM FOR AND METHOD OF TREATING A MALFUNCTIONING HEART

[75] Inventor: Todd J. Cohen, Baltimore, Md.

[73] Assignee: Leonard Bloom, Towson, Md. ; a part interest

[21] Appl. No.: 105,030

[22] Filed: Oct. 6, 1987

[51] Int. Cl.⁴ .............................................. A61N 1/00
[52] U.S. Cl. ................................................ 128/419 D
[58] Field of Search ........ 128/419 D, 419 PG, 419 P, 128/705, 696, 695, 786

[56] References Cited

U.S. PATENT DOCUMENTS

| | | | |
|---|---|---|---|
| 3,614,954 | 10/1971 | Mirowski et al. | 128/419 D |
| 3,942,536 | 3/1976 | Mirowski et al. | 128/419 D |
| 4,164,946 | 8/1979 | Langer | 128/419 D |
| 4,184,493 | 1/1980 | Langer et al. | 128/419 D |
| 4,202,340 | 5/1980 | Langer et al. | 128/419 D |
| 4,210,149 | 7/1980 | Heilman et al. | 128/419 D |
| 4,223,678 | 9/1980 | Langer et al. | 128/419 D |
| 4,254,775 | 3/1981 | Langer | 128/419 D |
| 4,291,699 | 9/1981 | Geddes et al. | 128/419 D |
| 4,295,474 | 10/1981 | Fischell | 128/697 |
| 4,300,567 | 11/1981 | Kolenik et al. | 128/419 D |
| 4,303,075 | 12/1981 | Heilman et al. | 128/419 PG |
| 4,316,472 | 2/1982 | Mirowski et al. | 128/419 D |
| 4,323,075 | 4/1982 | Langer | 128/419 D |
| 4,393,877 | 7/1983 | Imran et al. | 128/705 |
| 4,403,614 | 9/1983 | Engle et al. | 128/419 D |
| 4,407,288 | 10/1983 | Langer et al. | 128/419 PG |
| 4,427,011 | 1/1984 | Spurrell et al. | 128/419 D |
| 4,440,172 | 4/1984 | Langer | 128/419 D |
| 4,475,551 | 10/1984 | Langer et al. | 128/419 D |
| 4,523,595 | 6/1985 | Zibell | 128/419 D |
| 4,548,203 | 10/1985 | Tacker, Jr. et al. | 128/419 D |
| 4,548,209 | 10/1985 | Wielders et al. | 128/419 D |
| 4,559,946 | 12/1985 | Mower | 128/419 D |
| 4,572,191 | 2/1986 | Mirowski et al. | 128/419 D |
| 4,576,170 | 3/1986 | Bradley et al. | 128/419 D |
| 4,592,367 | 6/1986 | Imran | 128/706 |
| 4,614,192 | 9/1986 | Imran et al. | 128/419 D |
| 4,625,730 | 12/1986 | Fountain et al. | 128/419 D |
| 4,662,377 | 5/1987 | Heilman et al. | 128/419 D |
| 4,693,253 | 9/1987 | Adams | 128/419 D |
| 4,708,143 | 11/1987 | Schroeppel | 128/419 PG |

OTHER PUBLICATIONS

Mirowski et al., "Recent Clinical Experience with the Automatic Implantable Cardioverter-Defibrillator", *Medical Instrumentation*, vol. 20, pp. 285-291 (1986).

Mirowski, "The Automatic Implantable Cardioverter-Defibrillator: An Overview", *JACC*, vol. 6, No. 2, pp. 461-466 (Aug. 1985).

Mirowski et al., "The Automatic Implantable Defibrillator, Department of Medicine", Sinai Hospital of Baltimore, MD U.S.A., (Aug. 3, 1981).

Luceri et al., "Implantable Devices for the Treatment of Cardiac Arrythmias", *Cardiology Clinics*, vol. 3, No. 1, (Feb., 1985).

Cohen, "A Theoretical Right Atrial Pressure Feedback Heart Rate Control System to Restore Physiologic Control to the Rate-limited Heart", *PACE*, vol. 7 (Jul.-Aug., 1984).

*Primary Examiner*—Francis J. Jaworski
*Assistant Examiner*—George Manuel
*Attorney, Agent, or Firm*—Leonard Bloom

[57] ABSTRACT

A system for and method of treating a malfunctioning heart is based on hemodynamics. The mean arterial pressure (MAP) mean right atrial pressure (MRAP), mean right ventrical pressure (MRVP), mean left atrial pressure (MLAP), mean left ventrical pressure (MLVP) or mean central venous pressure (MCVP) is sensed. The long term mean baseline pressure is monitored and if the short term current mean pressure differs therefrom by a predetermined value, an indication of hemodynamic compromise, cardioversion/defibrillation is effected. In a second embodiment, the determination of whether the difference between mean baseline and mean current pressure is undertaken after a rate criteria (for example a heart rate above 155 b.p.m. has been met. In a third embodiment, the rate and pressure criteria both must exist at the same time, before cardioverting/defibrillation is initiated. In a fourth embodiment, a microprocessor is used. The system may be integrated with antitachycardia and/or antibradycardia pacemakers.

56 Claims, 17 Drawing Sheets

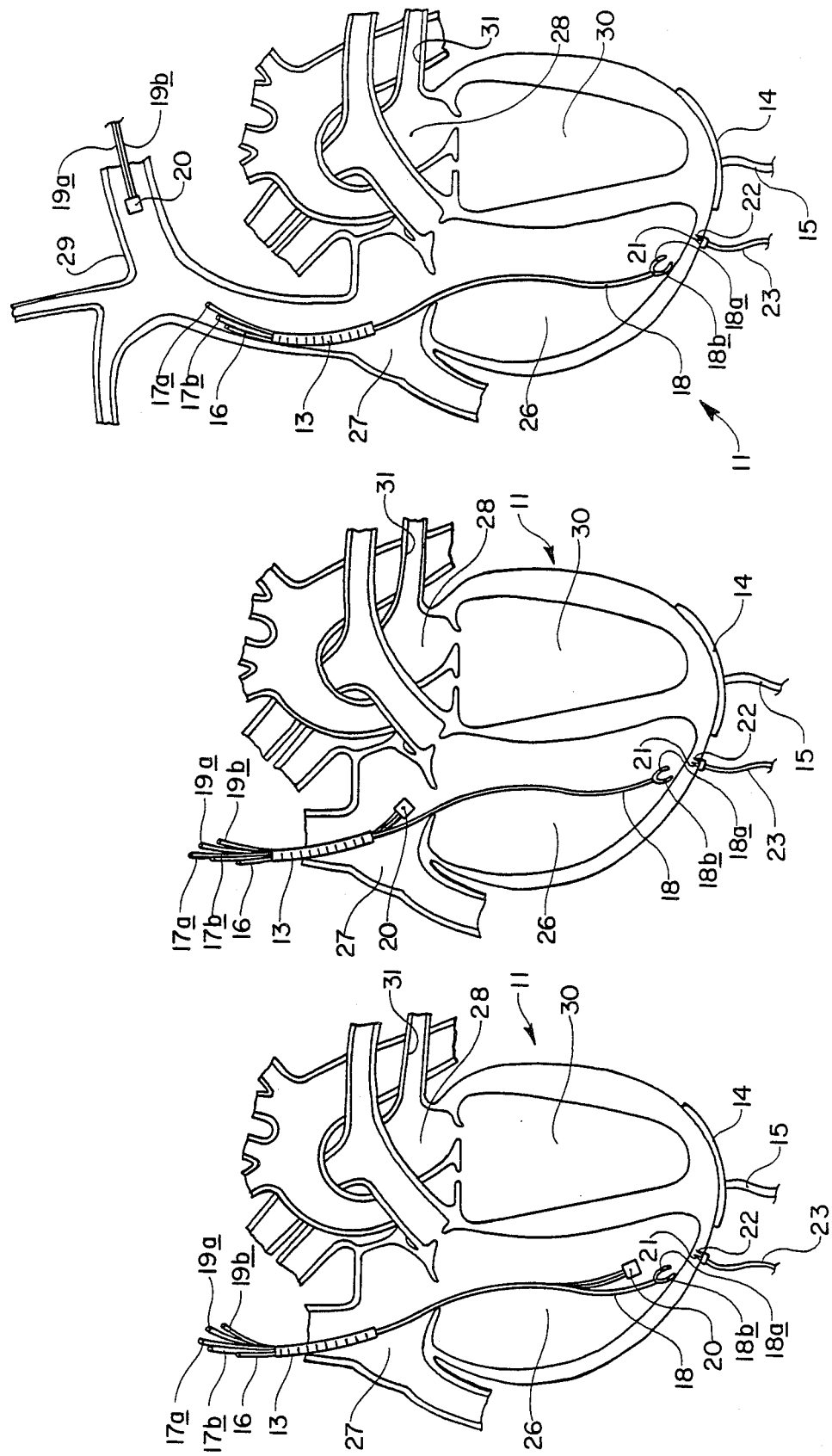

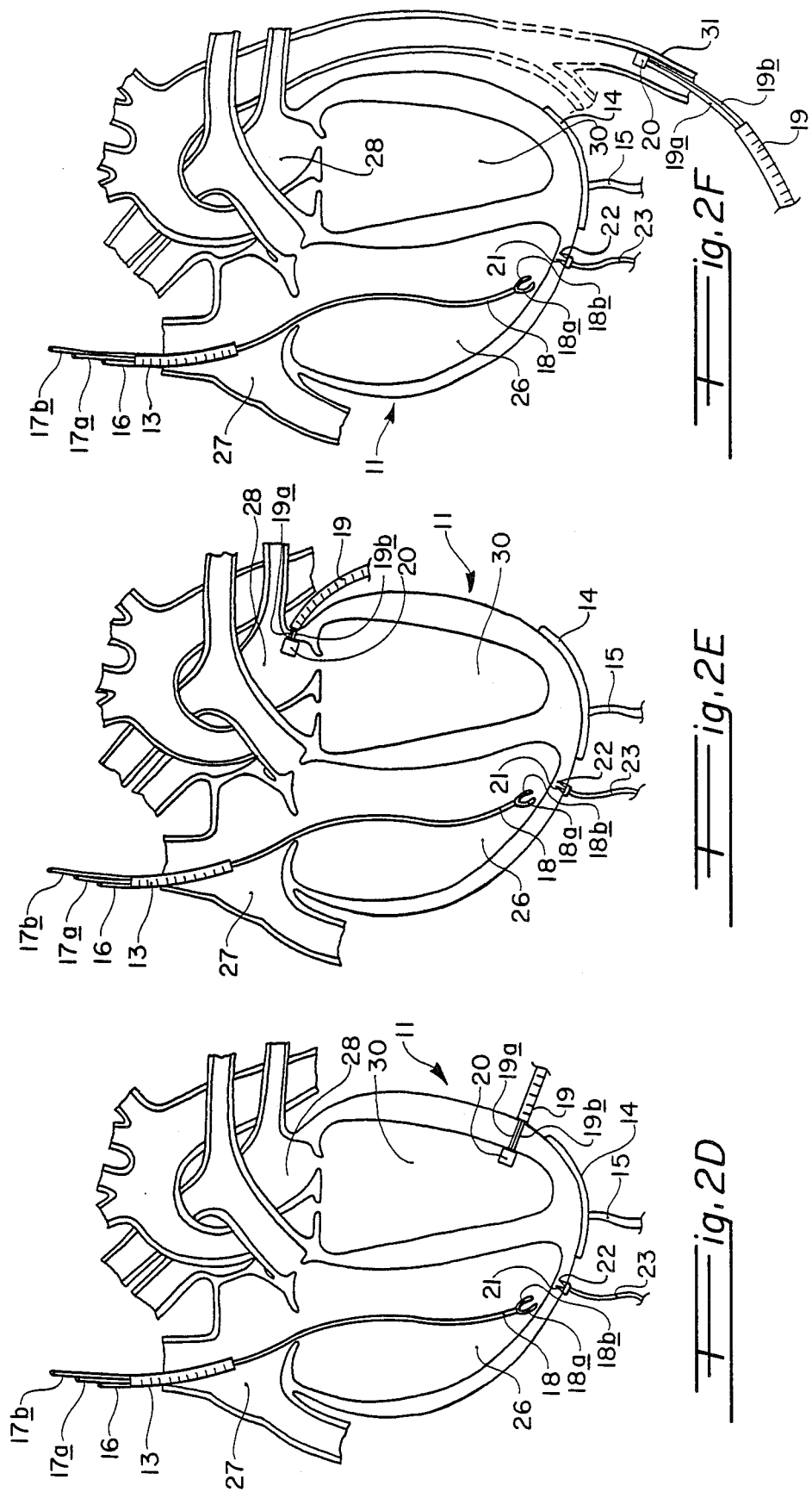

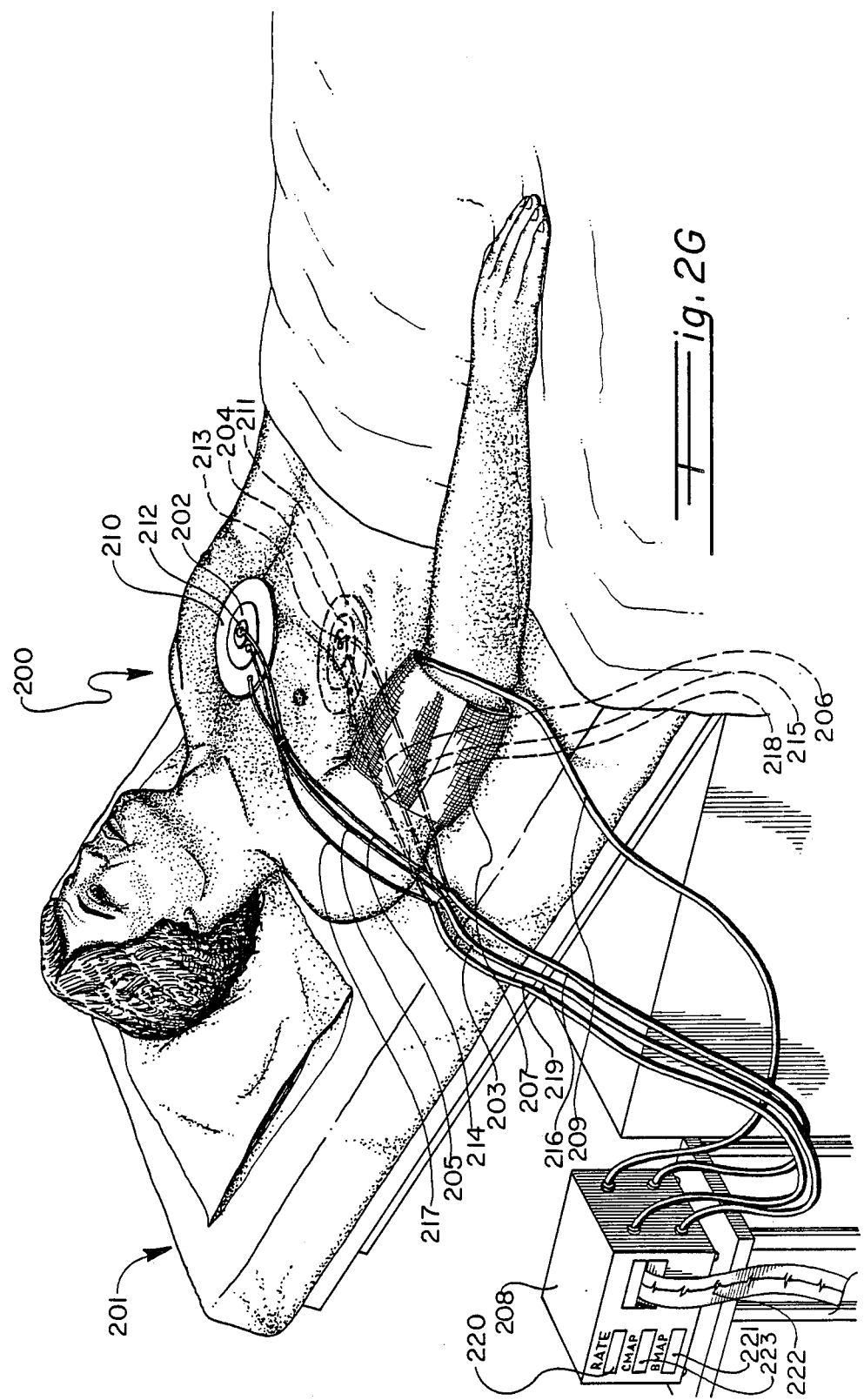

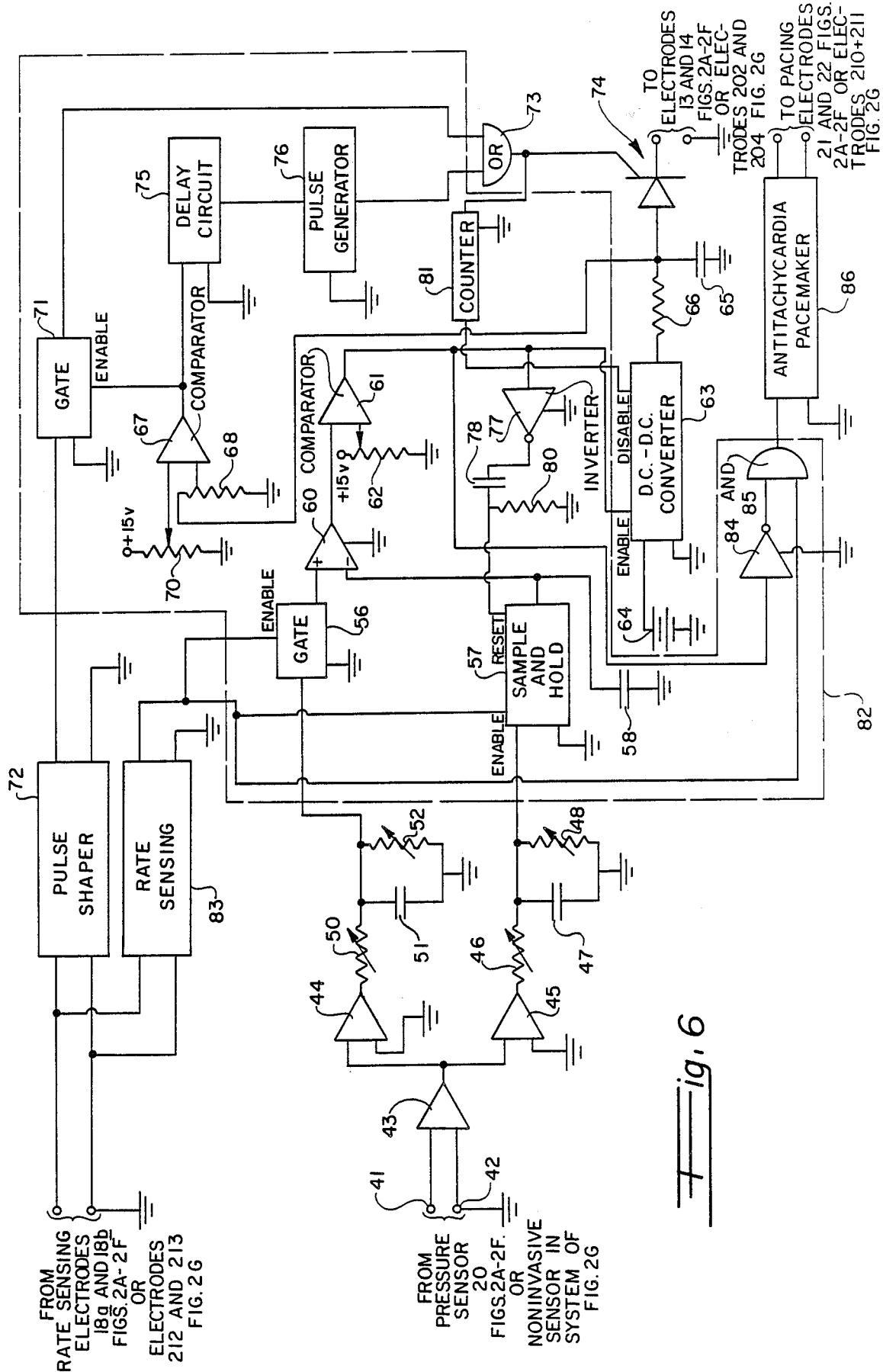

CONFER FIG. 7B

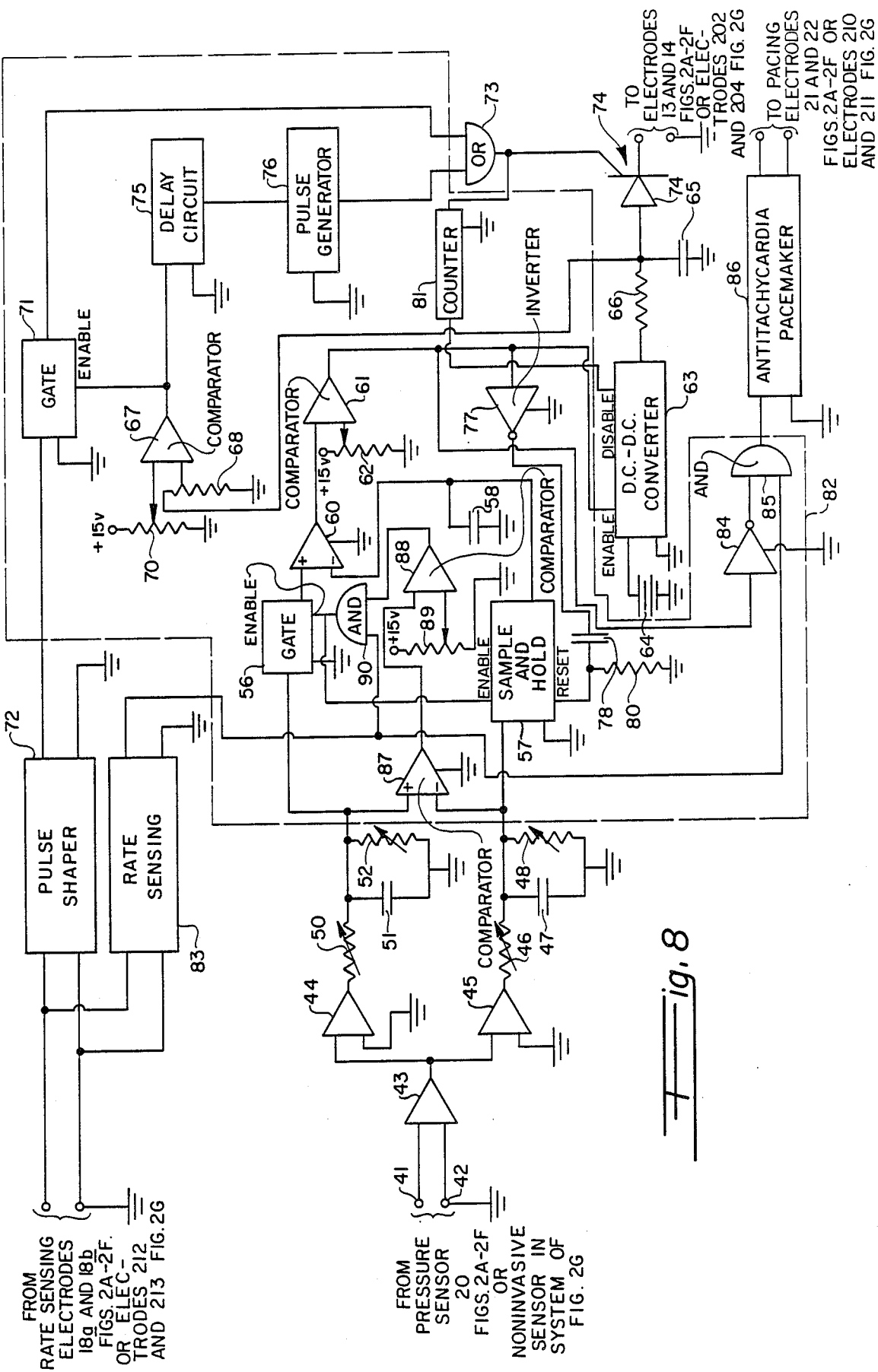

CONFER FIG. 9B

CONFER FIG. 9B

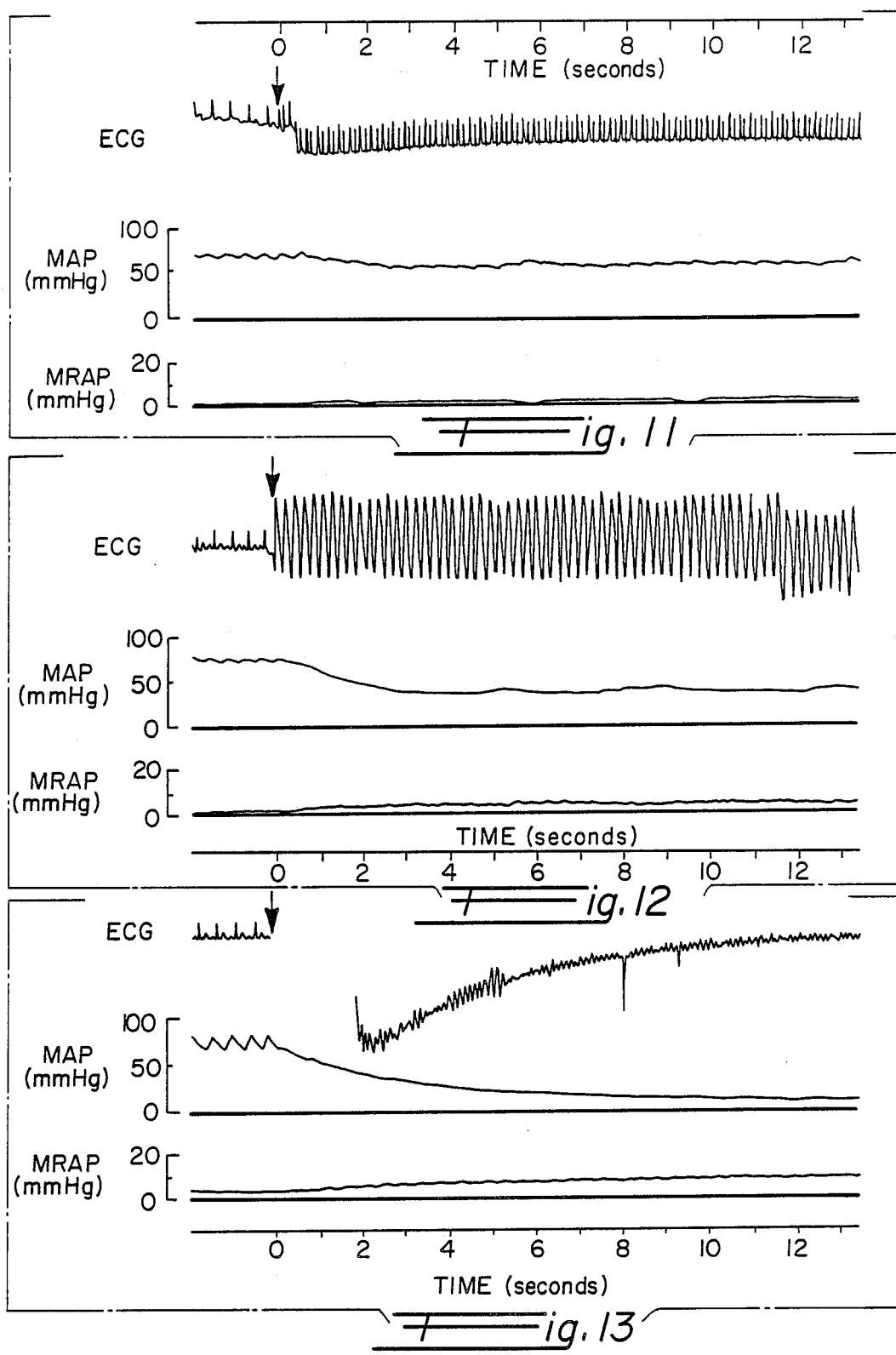

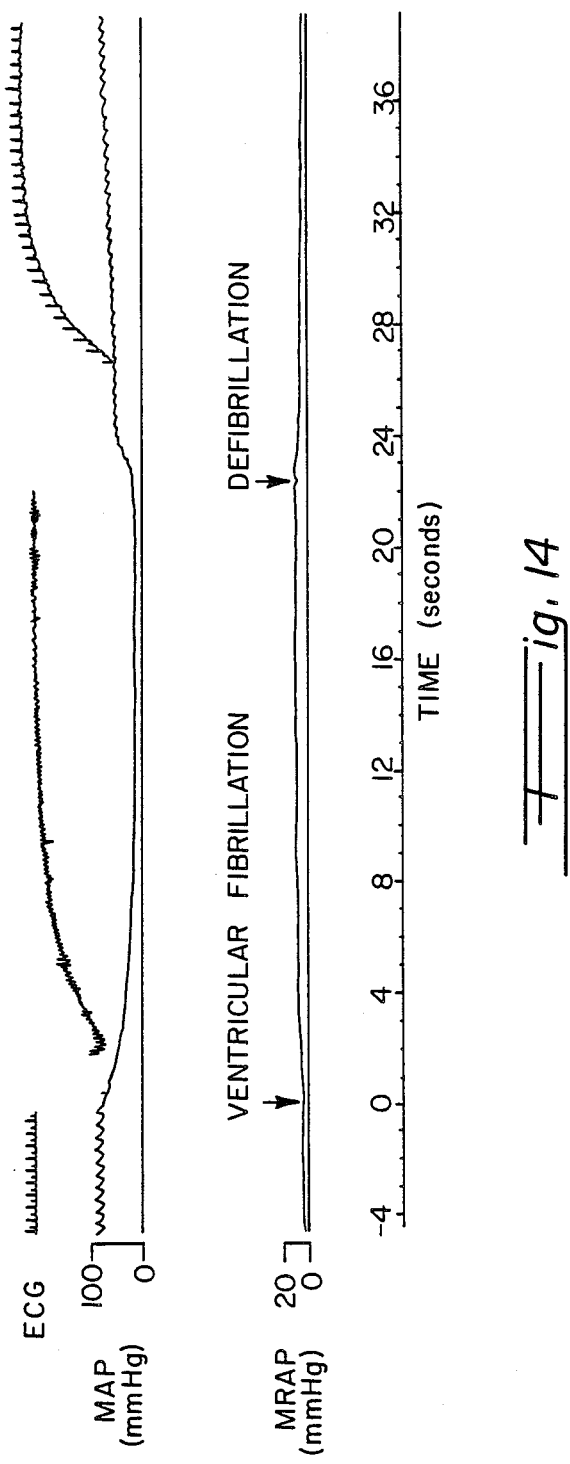

HEMODYNAMICALLY RESPONSIVE SYSTEM FOR AND METHOD OF TREATING A MALFUNCTIONING HEART

BACKGROUND OF THE INVENTION

1. Field of the Invention

This invention relates to a system for and method of treating a malfunctioning heart and, more particularly, to such a system and method which effects cardioversion/defibrillation in response to sensing a heart malfunction. The invention provides for the cardioverting/defibrillation of a malfunctioning heart as well as the possibility of overcoming a tachycardia manifestation without resorting to either cardioverting or defibrillating the heart.

2. Description of the Prior Art

In recent years, substantial progress has been made in pacemakers and in the development of cardioverting/defibrillating techniques for effectively treating various heart disorders and arrhythmias. Past efforts have resulted in the development of implantable electronic pacemakers and standby cardioverters-defibrillators which, in response to the detection of an abnormal cardiac rhythm, discharge sufficient energy via electrodes connected to the heart to depolarize and restore it to normal cardiac rhythm. An early example of this cardioverting/defibrillating technique is disclosed in U. S. Pat. No. 3,942,536 of Mirowski et al., the technique involving responses to a sensed peak right ventricular systolic pressure dropping to a fixed predetermined threshold level. This known technique did not involve mean pressure baselines, nor pressure changes in either direction therefrom.

Efforts have also been directed toward developing techniques for reliably monitoring heart activity in order to determine whether cardioversion/defibrillation are desirable or necessary. Such techniques include monitoring ventricular rate or determining the presence of fibrillation on the basis of a probability density function (PDF). A system using the PDF technique statistically compares the location of points of a cardiac waveform with the expected locations of points of the normal waveform. When the waveform becomes irregular, as measured by its probability density function, an abnormal cardiac function is suggested. The latter technique is described in U.S. Pat. Nos. 4,184,493 and 4,202,340 both of Langer et al.

A more recent system, as disclosed in U. S. Pat. No. 4,475,551 of Langer et al. utilizes both the PDF technique to determine the presence of an abnormal cardiac rhythm and a heart rate sensing circuit for distinguishing between ventricular fibrillation and high rate tachycardia (the latter being indicated by a heart rate above a predetermined minimum threshold), on the one hand, and normal sinus rhythm or a low rate tachycardia (indicated by a heart rate falling below a pre-determined minimum threshold), on the other hand.

Still further, research in this area has resulted in the development of a heart rate detector system which accurately measures heart rate from a variety of different electrocardiogram (ECG) signal shapes. One such system is disclosed in U.S. Pat. No. 4,393,877 of Imran et al.

Despite these past efforts and the level of achievement prevalent among prior art systems, there are potential difficulties and drawbacks which may be experienced with such devices.

Currently antitachycardia systems detect arrhythmias primarily by sensing rate and perform inadequately in the differentiation of hemodynamically stable from unstable rhythms. These devices, for example, may fire during a stable supraventricular tachycardia (SVT) inflicting pain and wasting energy; damage to the heart may result.

A commonly used implantable antitachycardia device is the automatic implantable cardioverter-defibrillators (AICD) which is commercially available under the model designations 1500, 1510 and 1520 from Cardiac Pacemakers, Inc. whose address is: 4100 North Hamlin Avenue, St. Paul, Minn. 55164. These devices continuously monitor myocardial electrical activity, detecting ventricular tachycardia (VT) and ventricular fibrillation (VF), and delivering a shock to the myocardium to terminate the arrhythmia. The AICD has been shown to reduce the mortality rate in patients with malignant arrhythmias with initial studies at Johns Hopkins Hospital and Stanford Medical Center demonstrating a 50 percent decrease in the anticipated total incidence of death, as reported by Mirowski et al., "Recent Clinical Experience with the Automatic Implantable Cardioverter-Defibrillator", *Medical Instrumentation*, Vol. 20, pages 285-291 (1986). Arrhythmias are detected by (1) a rate (R wave) sensor and (2) a probability density function (PDF) which defines the fraction of time spent by the differentiated electrocardiogram between two amplitude limits located near zero potential. Presently, the functional window of the PDF is wide to permit the detection of both VT and VF, and therefore, this device functions essentially as a rate-only sensing system. As reported by Mirowski, "The Automatic Implantable Cardioverter-Defibrillator: An Overview", *JACC*, Vol. 6, No. 2, pages 461-466, (August, 1985), when an arrhythmia fulfills either the rate or PDF criteria, the device delivers Schuder's truncated exponential pulse of 25 Joules some 17 seconds after the onset of the arrhythmia. The device can recycle as many as three times if the previous discharge is ineffective with the strength of the second, third and fourth pulses being increased to 30 Joules. After the fourth discharge, approximately 35 seconds of nonfibrillating rhythm are required to reset the device.

The Mirowski et al., supra, and the Mirowski, supra publications set out, in summary form, background material relating to the defibrillating/cardioverting arts against which the present invention was made.

In addition to the standard automatic implantable cardioverter-defibrillator characterized by the above-noted, dual detection algorithm, a variant of the device which features a sensing system that relies only on the analysis of heart rate is also available. This "rate-only" version of the known cardioverter-defibrillator preferred by some investigators, is more sensitive than the dual detection version unit and theoretically less likely to miss ventricular tachycardias with narrow QRS complexes. It is believed that the "rate-only" system, on the other hand, may be too sensitive, delivering cardioverting/defibrillating pulses too often or too soon, no hemodynamic parameter having been taken into consideration.

One problem with current systems is that they function primarily as a rate-only sensing systems and may fire for nonmalignant as well as malignant tachycardias. These firings are not benign; potentially endangering myocardium, wasting energy and inflicting pain on the conscious patient, all distinct shortcomings and disadvantages.

The principal object of the present invention is to provide a system for cardioverting/defibrillating which avoids unnecessary firings, thereby reducing the danger to the myocardium, saving energy and avoiding pain.

Another object of the present invention is to provide an implantable system for cardioverting/defibrillating which avoids unnecessary firings, thereby reducing the danger to the myocardium, saving energy and avoiding pain.

A further object of the present invention is to provide a system for cardioverting/defibrillating which is hemodynamically responsive to change in pressure from baseline mean pressure.

An additional object of the present invention is to provide a system for cardioverting/defibrillating which is hemodynamically responsive to change in baseline mean pressure and to rate criteria.

Yet another object of the present invention is to provide a method of cardioverting/defibrillating which may be advantageously carried out using a cardioverter-defibrillator constructed in accordance with the present invention.

Yet a further object of the present invention is to provide a method of cardioverting/defibrillating which avoids unnecessary firings thereby reducing the danger to the myocardium, saving energy and avoiding pain.

In accordance with preferred embodiments of the present invention, new sensing algorithms are proposed using hemodynamic or both hemodynamic and rate criteria, the latter being taken in series or parallel. The series configuration algorithm could be effected by detecting rate with an intracardiac, extracardiac, or body-surface R-wave sensor. When rate exceeds the programmed cut-off value, at least one hemodynamic parameter, such as departures from baseline mean right atrial pressure (MRAP), mean right ventricular pressure (MRVP), mean central venous pressure (MCVP) or mean arterial pressure (MAP) would be monitored. Mean left atrial pressure (MLAP) or mean left ventricular pressure (MLVP) may also be suitable as one or another of the hemodynamic baseline parameters from which changes may be monitored. If mean right arterial pressure (MRAP) or mean right ventricular pressure (MRVP) or mean central venous pressure (MCVP) increases from respective baseline MRAP or MRVP or MCVP baselines within a time period of predetermined duration, indicating hemodynamic compromise, the system would fire. If mean left atrial pressure (MLAP) or mean left ventricular pressure (MLVP) increases respectively from respective baseline MLAP or baseline MLVP within a time period of predetermined duration indicating hemodynamic compromise, the system would fire. If mean arterial pressure (MAP) decreases from baseline MAP beyond a predetermined magnitude indicating hemodynamic compromise the system would fire. If the respective pressure changes were less than the respective predetermined magnitudes, pressures would be monitored to determine if respective changes from the respective mean levels take place, as long as the rate criteria is satisfied. A parallel configuration algorithm in which rate and hemodynamic criteria function simultaneously is also proposed; however, continuous pressure change determination would probably be less energy efficient. Either configuration of algorithm could be adapted to a single catheter consisting of a pressure transducer in either the right atrium or right ventricle and an R-wave sensing electrode or pair of electrodes at the catheter tip in the right ventricle. The hemodynamic information derived from an arterial line, Swan-Ganz catheter (already present in the intensive/cardiac care unit patients), or even an automated mechanical blood pressure cuff could be integrated together with the electrocardiogram to provide a temporary automatic antitachycardia system. Cardioversion-defibrillation could be administered using externally applied patches. Even a noninvasive hemodynamically responsive antitachycardia system is potentially feasible using doppler technology for pressure measurements. The PDF (narrow window of function) and the rate/pressure sensing algorithm could be used simultaneously such that if the rate/pressure criteria are satisfied (indicating hemodynamically significant SVT or VT) the device cardioverters and if the PDF criteria is satisfied indicating (VF) defibrillation results. This pulse delivery system could also be incorporated into a single catheter.

It is to be appreciated that when the pressure criteria is not met, but the rate criteria indicates tachycardia is present, an antitachycardia pacemaker could be enabled in an effort to correct the malfunction.

MAP is an excellent parameter but accurate continuous measurement requires an indwelling arterial catheter or transducer which over time is prone to infection and thrombus formation (with the potential for systemic embolic events). MRAP and MRVP appear to relate useful information regarding the hemodynamic state of the particular arrhythmia. If tricuspid stenosis were present, MRVP would probably be more reliable than MRAP. Preliminary observations in the canine model suggest that changes as small as 3 mmHg for MRAP and MRVP and as small as 15 mmHg for MAP are significant and can be used in carrying out the present invention.

The rate/pressure sensing algorithms could also help integrate a cardioverter-defibrillator with an antitachycardia pacemaker. The hemodynamic function would determine which of these devices to engage. For example, when a hemodynamically significant tachycardia is detected the cardioverter-defibrillator would be used to terminate the arrhythmia. When a hemodynamically stable tachycardia is sensed the antitachycardia pacemaker would attempt to terminate the arrhythmia using such methods as overdrive, burst, or extra stimulus pacing, incremental or decremental scanning, or ultra-high frequency stimulation. If the tachycardia was accelerated, this would be detected by the rate/pressure sensing algorithm and cardioverted or defibrillated. With a pacemaker present, a bradycardia failsafe could be built into the system.

The adaptation of a hemodynamic parameter to the sensing system of antitachycardia devices appears to be a logical improvement to its present function. MRAP and MRVP are easily measured parameters (via the transvenous route) and appear to relate important hemodynamic information. MAP is an easily measured parameter in the intensive/cardiac care unit setting and could be integrated together with the electrocardiogram to form a temporary automatic antitachycardia system. A rate/pressure sensing algorithm, designed either in series or parallel, could be integrated with the PDF system such that hemodynamically significant SVT, VT, and VF would be detected. The rate/pressure sensing algorithm could also be applied to a combined cardioverter-defibrillator and antitachycardia pacemaker.

The present invention, from one vantage point, can be viewed as a system for treating a malfunctioning heart, the system including storage means for storing electrical energy. Pressure responsive sensing means is provided for sensing at least one hemodynamic parameter. Electrode means are utilized for electrically coupling the storage means to the heart. Means responsive to output from the sensing means charge and enable discharge of the electrical energy stored by the storage means across the electrode means and into the heart upon sensing a change in pressure of a predetermined amount from mean baseline pressure.

From a somewhat different vantage point, the invention can be seen as being a system for treating a malfunctioning heart, the system including means for sensing heart rate and producing a first control signal whenever the rate exceeds a predetermined rate. Pressure responsive means are provided for sensing at least one hemodynamic parameter and for producing a second control signal whenever the sensed hemodynamic parameter departs from mean baseline pressure by at least a predetermined amount. Controllable antitachycardia pacemaking means is provided to supply pacing signals to the heart, if needed. Controllable cardioverting/defibrillating means including storage means for storing electrical energy and electrode means are provided to apply electrical energy from the storage means to the heart to cardiovert or to defibrillate same, if needed. Control circuit means respond to the first control signal and to the second control signal for enabling the antitachycardia pacemaking means whenever both the first control signal is present and the second control signal is absent and for enabling said cardioverting/defibrillating means whenever the first control signal and the second control signal are present. Means are arranged to discharge the electrical energy stored by the storage means across the electrode means and into the heart.

The pressure responsive sensing means for sensing at least one hemodynamic parameter may include signal processing means for determining mean right atrial pressure (MRAP), mean right ventricular pressure (MRVP), mean central venous pressure (MCVP), mean left atrial pressure (MLAP), mean left ventricle pressure (MLVP) or mean arterial pressure (MAP) may be provided.

The signal processing means for determining mean pressure may include means for providing a control signal whenever the mean pressure departs from mean baseline pressure by at least a predetermined amount. The means responsive to output from the sensing means for charging and enabling discharge is coupled to the signal processing means and is responsive to the output control signal.

The signal processing means for determining mean pressure may include means for providing an output control signal whenever the current mean pressure or instant pressure increases, in all but the case in which arterial pressure is involved, a predetermined amount from baseline mean pressure. The means responsive to output from the sensing means for charging and enabling discharge is coupled to the signal processing means and is responsive to the control signal.

In those cases where the pressure responsive sensing means for sensing at least one hemodynamic parameter includes signal processing means for determining baseline mean arterial pressure, departures in current mean pressure or instant pressure from the mean baseline pressure is in a decreasing direction.

The system may include a microprocessor for developing control signals to control the application of electrical energy to the heart, as well as controlling an antitachycardia pacemaker.

From a slightly different vantage point, the invention can be seen as a system for treating a malfunctioning heart, the system including means for providing cardioverting/defibrillating electrical energy and pressure responsive sensing means for sensing at least one hemodynamic parameter. Means responding to output from the sensing means deliver the cardioverting/defibrillating electrical energy into the heart upon sensing a change in instant pressure or current mean pressure of a predetermined magnitude from mean baseline pressure.

The invention can also be seen as a system for treating a malfunctioning heart, the system including means for sensing heart rate and producing a first control signal whenever the rate exceeds a predetermined rate. Pressure responsive means is provided for sensing at least one hemodynamic parameter and for producing a second control signal whenever the sensed hemodynamic parameter departs from mean baseline pressure by at least a predetermined amount. Controllable antitachycardia pacemaking means is provided to supply pacing signals to the heart. Controllable cardioverting/defibrillating means produce cardioverting/defibrillating electrical energy. Control circuit means, respond to the first control signal and to the second control signal and enable the antitachycardia pacemaking means whenever both the first control signal is present and the second control signal is absent. The control circuit means enable the cardioverting/defibrillating means whenever the first control signal and the second control signal are present.

The invention can be viewed as being in a system for treating a patient having a malfunctioning heart which includes means responsive to at least one control signal for supplying the patient with malfunction-correcting input. The system is improved by pressure responsive means for sensing at least one hemodynamic pressure parameter. The control signal is produced upon sensing a change in pressure of a predetermined amount from mean baseline pressure. The input may be electrical signals and/or electrical energy delivered to the malfunctioning heart.

The invention is, from another vantage point, a system for treating a patient having a malfunctioning heart which includes means responsive to at least two control signals for supplying the patient with malfunction-correcting input. Pressure responsive means are provided for sensing at least one hemodynamic pressure parameter to produce one of the two control signals upon sensing a change in pressure of a predetermined amount from mean baseline pressure. Means responsive to heart rate produce the second of the two control signals. The input may be electrical signals and/or electrical energy delivered to the malfunctioning heart.

In its method aspect, the invention may be viewed as a method of treating a malfunctioning heart, the method including the step of sensing at least one parameter of heart activity. In accordance with a salient feature of the invention, the improvement includes sensing change in at least one hemodynamic pressure parameter from a mean baseline pressure, and thereafter delivering cardioverting/defibrillating electrical energy to the heart in response at least to change of predetermined magnitude in the sensed hemodynamic pressure parameter from the mean baseline pressure. Thus, a malfunction susceptible to correction by delivering electrical energy to the heart is corrected.

The step of sensing change in at least one hemodynamic parameter may include determining change in or from mean baseline right atrial pressure (MRAP), mean baseline right ventricle pressure (MRVP), mean baseline central venous pressure (MCVP), mean baseline left atrial pressure (MLAP) or mean baseline left ventricular pressure (MLVP) in an increasing direction, and, if desired, sensing heart rate, the step of delivering cardioverting/defibrillating electrical energy being taken only when the heart rate (if this be a selected criteria) exceeds a given rate and/or the change in or from mean baseline pressure exceeds the predetermined magnitude. If the heart rate is not a selected criteria, the step of delivering the electrical energy would be taken when the change in pressure from mean baseline pressure has been sensed, regardless of the heart rate.

The step of sensing change in at least one hemodynamic parameter may include determining change in or from mean baseline arterial pressure in a decreasing direction. The step of sensing the heart rate could be used, in the case of arterial pressure change, as an additional criteria.

In its method aspect the invention can be seen as being in an improvement in a method of treating a patient having a malfunctioning heart, which includes sensing change in at least one hemodynamic pressure parameter from a mean baseline pressure; and delivering to the patient malfunction-correcting input in response at least to change of predetermined magnitude in the sensed hemodynamic pressure parameter from the mean baseline pressure. This improved method may include sensing heart rate, the step of delivering to the patient being taken when the heart rate exceeds a given rate and the change in mean pressure from mean baseline pressure exceeds the predetermined magnitude. The step of delivering input to the patient may involve delivering electrical signals and/or electrical energy to the malfunctioning heart.

The novel features that are considered characteristic of the invention in its method and system aspects are set forth with particularity in the appended claims. The invention itself, however, both as to its organization and its method of operation, together with other objects and advantages thereof is to be understood from the following description of illustrative embodiments, when read in conjunction with the accompanying drawings, wherein like reference numerals refer to like components.

BRIEF DESCRIPTION OF THE DRAWINGS

FIG. 2A is an illustration of one catheter, which may be used in practicing the present invention, positioned within a heart, a pressure responsive sensor forming part of the catheter being shown positioned inside the right ventricle.

FIG. 2B is an illustration of a second catheter, which may be used in practicing the present invention, positioned within a heart, a pressure responsive sensor forming part of the catheter being shown positioned within the right atrium.

FIG. 2C is an illustration of a third catheter, which may be used in practicing the present invention, positioned within the left side of the heart, a pressure responsive sensor being shown positioned within a major vein feeding into the superior vena cava.

FIG. 2D is an illustration of a fourth catheter, which may be used in practicing the present invention, positioned within the left side of the heart, a pressure responsive sensor being shown positioned within the left ventricle.

FIG. 2E is an illustration of the fourth catheter positioned within the left side of the heart, a pressure responsive sensor being shown positioned within the left atrium.

FIG. 2F is an illustration of the fourth catheter positioned within the left side of the heart, a pressure responsive sensor being shown positioned at a point in the arterial system.

FIG. 2G is an illustration of a variant in which an external blood pressure cuff is provided to sense arterial pressure, from which MAP can be derived.

FIG. 6 is a partially block, schematic diagram of a hemodynamically responsive system for treating a malfunctioning heart in accordance with a second exemplary embodiment of the invention which is pressure and rate responsive.

FIG. 8 is a partially block, schematic diagram of hemodynamically responsive system for treating a malfunctioning heart which is a variant of the circuit of FIG. 6.

FIGS. 11–13 are respective graphical representations along a time axis of a rate wave (R-wave), mean arterial pressure (MAP) and mean right atrial pressure (MRAP) of a canine subject respectively under high right atrial pacing, right ventricle apex pacing and in ventricular fibrillation, useful in understanding the present invention.

FIG. 14 is a graphical representation along a time axis similar to the graphical representation of FIG. 13, the time base having been expanded to show the affects on the R-wave, the MAP and MRAP which result from successful defibrillation.

DETAILED DESCRIPTION OF THE PREFERRED EMBODIMENTS

Figure 1:
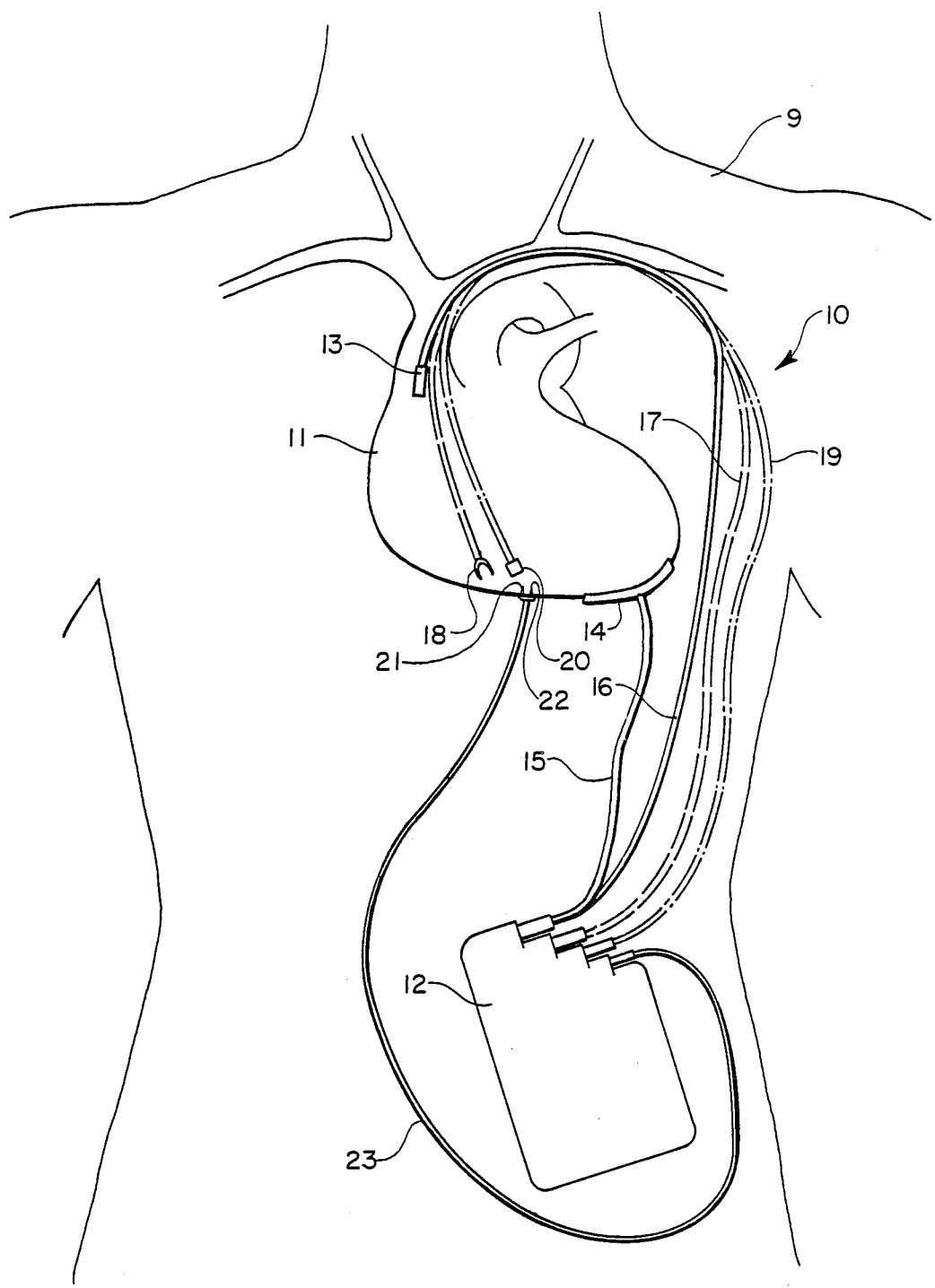
FIG. 1 is a diagrammatic, generalized illustration of an exemplary, implanted hemodynamically responsive system for treating a malfunctioning heart.

As shown in FIG. 1, an exemplary embodiment of an automatic implantable cardioverter-defibrillator system is designated generally by the numeral 10 and illustrated diagrammatically as being implanted within a human subject 9. The cardioverter-defibrillator system 10 includes an implanted housing 12 within which major circuit components of the system are housed. A first electrode 13 is positioned within the heart 11 of the subject 9, the details of placement and nature of the first electrode being more specifically shown in FIGS. 2A-2F to which reference is to be made below. A second electrode, illustrated as a patch electrode 14 is positioned on the outside of the heart 11 at the apex thereof. The pair of electrodes 13, 14 are provided for the purpose of delivering D.C. cardioverting/defibrillating energy from within the housing 12 to the heart 11 under control of circuitry within the housing, a pair of insulated leads 16 and 15 respectively being provided for this purpose. A pair of rate sensing electrodes 18 are provided within the heart 11, these electrodes being positioned in tissue and being conductively coupled to circuitry within the housing 12 via an insulated cable 17. A further pair of leads extend from a pressure responsive pressure-to-voltage transducer 20 to circuitry within the housing 12 via an insulated cable 19. It is to be understood that the insulated leads 15 and 16, the insulated cable 17 (or the pair of leads therein), and the insulated cable 19 (or the pair of leads therein) can all be incorporated into a single cable, the electrode 13, the rate sensing electrodes 18 and the pressure transducer 20 being carried by and forming parts of a catheter.

Pacemaking circuitry within the housing 12 may be provided to produce antitachycardia pacemaking signals, to a pair of pacing electrodes 21 and 22, illustrated as being fixed in tissue on the right-side of the heart. The pacing electrodes 21 and 22 are connected by respective conductive leads within a cable 23 which communicates with circuitry within the housing 12.

Turning to FIG. 2A, a more detailed illustration of the heart 11 of a subject, shows the heart in somewhat more detail and in section so that placement of parts of the system within the heart 11 can be seen in more detail, albeit diagrammatically. The heart 11 as illustrated includes a right ventricle 26, a right atrium 27, a left atrium 28 and a left ventricle 30. The electrode 13 is positioned within the superior vena cava. It is to be understood that the patch electrode 14, which cooperates with the electrode 13, could also be modified into a different form so it too could be positioned within the heart. The electrode 13 could be replaced with a patch electrode so that it also could be positioned on the surface of the heart, without departing from the present invention. The electrodes 13 and 14, in cases not involving implantation, could be replaced with conventional paddle electrodes or other external, body engaging electrodes, again without departing from the present invention. Thus, the invention could be used as a temporary measure for patient care in intensive care units and the like.

As illustrated in FIG. 2A, the pacing electrodes 21 and 22 are shown as being positioned on the exterior wall of right ventricle 26 for the purpose of illustration; these pacing electrodes could be placed elsewhere on or within the heart 11 in accordance with the needs of individual patients, taking into account the best particular location most suitable for correcting or overcoming the particular malfunction involved, the condition of the individual patient and his or her heart being taken into account.

Heart rate wave (R-wave) sensing electrodes 18a and 18b are illustrated as being positioned near the apex of the heart 11 within the right ventricle 26, for purposes of illustration. Other locations are equally well suited; again, the selected location being chosen with the condition of the particular patient and his or her heart in mind. The electrodes 18a and 18b are conductively connected to the circuitry within the housing 12 via leads 17a and 17b within the cable 17.

The pressure-to-voltage transducer 20, as illustrated in FIG. 2A, is positioned within the right ventricle 26. Two conductive leads 19a and 19b within the cable 19 (FIG. 1) provide electrical communication from the pressure responsive transducer 20 to circuitry within the housing 12 (FIG. 1). Thus, a D.C. voltage signal representative of the actual, instant pressure within the right ventricle 26 is fed to the circuitry within the implanted housing 12 (FIG. 1).

As illustrated in FIGS. 2B-2F, the heart 11, as well as the components of the system of the present invention, other than the pressure-to-voltage transducer 20, correspond to the heart 11 and the system components as shown in FIG. 2A. The placement of the transducer 20 differs, in each of FIGS. 2B-2F. As shown in FIG. 2A, the transducer 20 provides, as its output, a variable D.C. voltage representative of the varying pressure within the right ventricle 26 (a site in a circulatory system). As shown respectively in FIGS. 2B-2E, the transducer 20 is positioned within and produces a variable D.C. voltage which represents respectively the pressure within the right atrium 27 (a site in a circulatory system), within the central venous system (in particular, a major vein 29, a site in a circulatory system), the left ventricle 30 (a site in a circulatory system), the left atrium 28 (a site in a circulatory system) and the arterial system (in particular, an artery 31, a site within a circulatory system, remote from the heart 11).

In FIG. 2G a portion of a noninvasive system for sensing heart rate and pressure of the type which may be used in an intensive care unit (ICU), a recovery room, coronary care unit (CCU), and/or in a routine care patient facility is illustrated. The system of FIG. 2G can be considered a system which can be substituted for the invasive systems shown in FIGS. 1 and 2A-2F. A patient 200 is shown in a reclined posture on a bed 201. A pair of pulse-delivering electrodes 202 and 204 (substitutes for electrodes 13, 14; FIGS. 2A-2F) are positioned respectively on the anterior and posterior chest of the patien 200 for the purpose of coupling cardioverting/defibrillation energy pulses to the patient, respective insulated leads 205 and 206 (substitutes for leads 15, 16; FIGS. 2A-2F) and a cable 203 being provided to conduct the pulses to the patient, from a pulse-generating apparatus 208 (substitute for the circuitry within housing 12; FIG. 1). The leads 205 and 206 and electrodes 202 and 204 are to be used in place of the cardioverting/defibrillating electrodes 13 and 14 (FIGS. 1 and 2A-2F), were the system of the present invention to be used in a noninvasive stand-alone or portable or patient-carried configuration, instead of in an implantable configuration as illustrated in FIGS. 1 and 2A-2F. Positioned concentrically about the respective electrodes 202 and 204 and insulated therefrom, are respective pacing electrodes 210 and 211 (substitutes for 21, 22; (FIGS. 1, 2A-2F). A pair of respective rate (R-wave) sensing electrodes 212 and 213 (substitutes for electrodes 18, FIG. 1; 18a, 18b, FIGS. 2A-2F) are provided centrally within and insulated from the electrodes 202 and 204, respectively. The pair of rate-sensing electrodes 212, 213 are connected respectively via respective insulated leads 214, 215 and a cable 216 to the apparatus 208. The pair of pacing electrodes 210, 211 are connected respectively via respective insulated leads 217, 218 and a cable 219 to the apparatus 208.

Moreover, rather than an invasive pressure transducer of the type illustrated in FIGS. 1 and 2A-2F, the system may be modified to sense, in a noninvasive fashion, arterial pressure using a conventional cuff 207 removably fixed to, as shown, the right upper arm of the patient 200, the sensed pressure-related electrical signals being produced by a conventional transducer within the apparatus 207. A pneumatic tube or conduit 209 is provided both to supply automatically and intermittantly compressed air to the cuff 207 and to receive either audible sounds (which are processed within the apparatus 208 to derive MAP representing data) or an electrical output from a transducer positioned within the cuff 207. The transducer produces electrical output signals which appears on a pair of conductive leads within the conduit 209. The cuff 207 is supplied, as is conventional, intermittantly with compressed air via the air conduit 209. The components illustrated in FIG. 2G are used to monitor arterial blood pressure intermittantly, for example once for a short period every 30 seconds. The pressure data so developed can be used to develop long-term mean baseline pressure-related signals and short-term (current) mean pressure-related signals. Such intermittantly developed inputs can, as will be readily understandable by persons skilled in the art, be used in place of the inputs provided from the pressure sensing transducer 20 (FIGS. 1, 2A-2F) to derive pressure- and heart rate- representing input signals for use in conjunction with the circuits discussed hereinbelow. The apparatus 208 may be provided with a heart rate display 220, baseline MAP display 221, and a current MAP display 223. An EKG strip recording 222 could be produced by the apparatus from a connection electrode arrangement (now shown) which could include the rate (R-wave) sensing electrodes 212 and 213.

Figure 3:
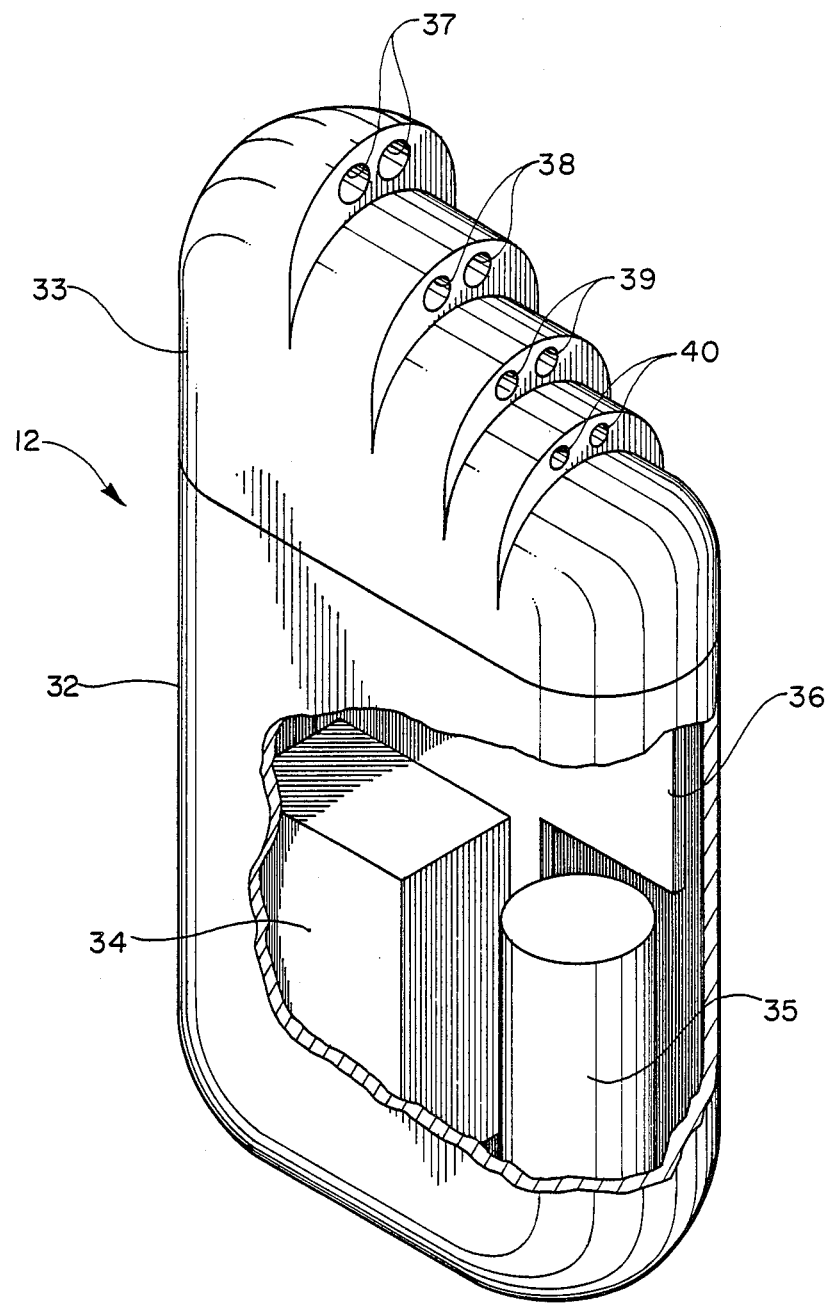
FIG. 3 is a pictorial illustration of an exemplary implantable controllable cardioverting/defibrillating electrical energy generator which may be used in practicing the present invention, the housing of the generator being partially broken away to show positioning of major components thereof.

One possible general implantable configuration of the housing 12 is shown in FIG. 3. The housing 12 includes a case 32, made of titanium, and a header 33, formed of an epoxy material, fixed to the case 32, all external components being hermetically sealed and biocompatible for human implantation. Within the case 32 is a battery pack or battery 34, an energy storage capacitor 35 and an electronic module 36 in or on which circuit components, other than the battery pack or battery 34 and the capacitor 35, are positioned. Detailed embodiments of exemplary circuits which are in or on or connected to the module 36 are illustrated in FIGS. 4, 6, 8 and 10, to which reference is made hereinbelow. A plurality of pairs of receptacles 37-40 are shown in the header 33 for receiving corresponding pairs of leads which are respectively within the insulated cables 15, 16 and 17 and 19 and 23 (FIG. 1).

Figure 4:
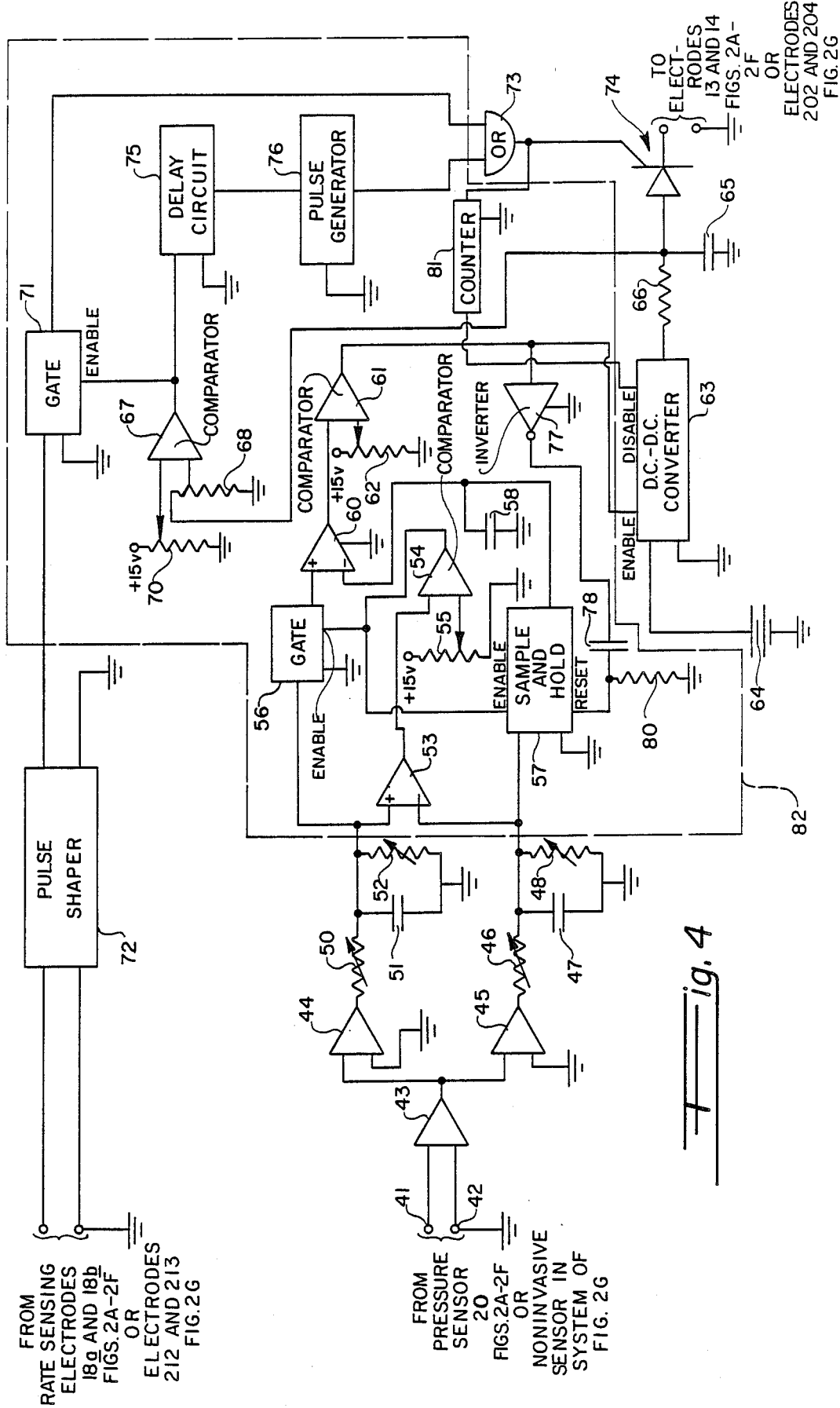
FIG. 4 is a partially block, schematic diagram of a hemodynamically responsive system for treating a malfunctioning heart in accordance with a first exemplary embodiment of the invention which is pressure responsive.

Turning to FIG. 4, a first exemplary embodiment of the circuit components, which may be positioned within the housing 12 (FIGS. 1 and 3) or the bed-side apparatus 208 (FIG. 2G), includes a pair of input terminals 41, 42 which receive the variable D.C. voltage output signal representing pressure from the pressure responsive transducer 20 (FIGS. 1 and 2A-2F) or noninvasive transducer (in system of FIG. 2G), the terminal 42 being connected to a point of circuit reference potential (ground). The terminals 41, 42 are connected to an amplifier 43, which amplifies the pressure representing D.C. input signal and feeds the same to respective buffer amplifiers 44 and 45. The circuit of FIG. 4 is suitable for practicing the present invention using a pressure-only criteria.

The output from the buffer amplifier 45 is supplied to an RC circuit constituted by an adjustable resistor 46 connected to ground via a series connected storage capacitor 47 having a large adjustable resistor 48 connected in parallel therewith. The time constants (charging and discharging) of these circuit components are such that the D.C. voltage across the capacitor 47 represents the mean pressure sensed by the transducer 20 (FIGS. 1 and 2A-2F) or a noninvasive transducer (in system of FIG. 2G) over a relatively long period, for example during the preceding fifteen (15) minutes or even longer (for example a number of hours) or shorter (for example one hundred twenty (120) seconds) being suitable in some cases. The resistors 46 and 48 may be set by a medical professional to suit the particular patient involved, so far as what the most suitable period length (period of predetermined length) for baseline data acquisition appears to be most suitable. The D.C. voltage level (first signal) across the capacitor 47 thus represents a long term mean baseline pressure. The term "mean" as used herein is broad and includes the average value as well as values near the average. The output from the buffer amplifier 44 is supplied to a second RC circuit constituted by an adjustable resistor 50 connected to ground via a capacitor 51, which has an adjustable resistor 52 connected in parallel therewith. The time constants (charging and discharging) of the circuit components are such that the D.C. voltage (second signal) which appears across the capacitor 51 represents the short term mean pressure sensed by the transducer 20 (FIGS. 1 and 2A-2F) or the noninvasive transducer (in system of FIG. 2G) over a relatively short period, for example, during the preceding fifteen (15) seconds or longer (for example 60 seconds) or shorter (for example six seconds). The resistors 50 and 52 may be set by a medical professional to suit the particular patient involved, so far as what the most suitable period length (period of given length) for current data acquisition appears to be most suitable.

As illustrated the long term (baseline) and short term (current) D.C. voltage signals which appear across the respective capacitors 47 and 51 are fed respectively to the inverting and noninverting terminals of an operational amplifier 53, a difference D.C. voltage signal appearing as the output from the operational amplifier 53. As shown, the inverting and noninverting terminals of the operational amplifier 53 are connected as they would be were pressures other than arterial pressures to be involved. Were MAP to be the hemodynamic parameter involved, the terminals would be reversed. The D.C. output signal from the operational amplfifier 53 is fed to a first input terminal of a first comparator 54, the second input terminal of the comparator 54 is connected to the wiper of a potentiometer 55 which is connected between ground and a point of fixed D.C. potential, illustrated as being +15 volts, from an internal power supply bus.

Whenever the voltage supplied to the comparator 54 from the operational amplifier 53 exceeds the voltage supplied via the wiper from the potentiometer 55, a low (ZERO) level on the output terminal from the comparator 54 goes high (ONE), the ONE signal being coupled as an enabling input to a gate 56 and to a sample-and-hold circuit 57 which receive, at their respective signal input terminals, the voltage representing current mean pressure appearing across the capacitor 51 and the voltage representing mean baseline pressure appearing across the capacitor 47.

A D.C. output from the sample-and-hold circuit 57 is stored in a storage circuit, for the purpose of illustration shown as a capacitor 58. This stored voltage signal representing mean baseline (long-term) pressure is supplied to the inverting input terminal of an operational amplifier 60 which has its noninverting input terminal connected to the output terminal of the gate 56, which when enabled, passes the D.C. voltage signal (stored first signal) appearing across the capacitor 51 and representing current (short-term) mean pressure to the operational amplifier 60. As illustrated, the inverting and noninverting terminals of the operational amplifier 60 are shown as they would be connected were pressures other than arterial pressure involved. Were MAP to be the hemodynamic parameter selected, the terminals would be reversed. The output from the operational amplifier 60 is supplied to an input terminal of a comparator 61, which has its other input connected to the wiper of a potentiometer 62 connected between ground and the +15 volt power supply bus. Whenever the voltage supplied to the comparator 61 from the operational amplifier 60 exceeds the voltage supplied from the potentiometer 62, an indication of hemodynamic compromise, the output terminal of the comparator 61 goes from low (ZERO) to high (ONE) which signal is passed to the enable terminal of a D.C.-to-D.C. converter 63. It is to be understood that the wipers of the potentiometers 55 and 62 are independently adjustable; consequently, the wiper on the potentiometer 62 may be positioned so that the pressure difference which causes its output to go from ZERO to ONE is slightly greater than pressure difference which causes the comparator 54 to initiate the enabling functions. The D.C.-to-D.C. converter 63, when enabled, receives current from a low voltage battery pack or battery 64 and converts it into a high D.C. voltage, for example a voltage of 720 volts, which is used, when the converter is enabled, to charge an energy storage capacitor 65, via a resistor 66 towards the high voltage. The capacitor 65 is of such size that it will store energy levels sufficient to produce the desired cardioverting/defibrillation pulses. The desired pulse is a truncated exponential pulse of about 25 Joules delivered approximately 17 seconds from onset of the hemodynamic compromise. The pulse could, especially when defibrillation is being undertaken after a failed attempt to cardiovert, be delivered somewhat later and with a higher energy level.

Once the capacitor 65 is charged to a sufficiently high D.C. voltage level to provide sufficient energy to effect cardioversion, as determined by a comparator 67, which receives on one input terminal a voltage proportional to the increasing D.C. voltage across the capacitor 65, a highly resistive voltage divider 68 being in parallel to the capacitor 65. The second input terminal of the comparator 67 is connected to the wiper of a potentiometer 70 which is connected between ground and the +15 volt bus. When the voltage across the energy storing capacitor 65 is sufficient to supply a cardioverting energy pulse to the malfunctioning heart, the voltage supplied to the one input terminal of the comparator 67 exceeds the voltage supplied to its other input terminal from the potentiometer 70 via its associated wiper. Under these conditions, the output from the comparator 67 goes from low (ZERO) to high (ONE), which ONE signal effects an enabling of an analog gate 71. The gate 71 has its signal input connected to receive an output from a pulse shaper 72, which receives an input from the rate sensing electrodes 18a, 18b (FIGS. 1 and 2A-2F) or from the rate sensing electrodes 212, 213 (FIG. 2G) and produces a pulse train in synchronism with the R-wave supplied from the electrodes 18a, 18b or electrodes 212, 213. If the pulse train from the pulse shaper 72 is present, these pulses are passed, via the gate 71, to an OR circuit 73 and thence to the gate electrode of an SCR 74. The first of these pulses which, if present, appears on the gate electrode fires the SCR 74 thereby discharging the energy then stored on the capacitor 65 into the malfunctioning heart, via the electrodes 13 and 14 (FIGS. 1 and 2A-2F) or the electrodes 202 and 204 (FIG. 2G) in an effort to effect cardioversion, the discharge being in synchronism with the R-wave.

In the event that the pulse shaper 72 does not produce a pulse to fire the SCR 74 because of the absence of an R-wave, the ONE signal from the comparator 67 is passed, via a delay circuit 75, which provides a delay of about three seconds or more and enables a pulse generator 76 causing it to produce an output pulse to initiate defibrillation which is supplied, via the OR circuit 73, to the gate electrode of the SCR 74 causing the SCR to fire. The energy storage capacitor 65, which by then has charged to a higher level discharges, via the SCR 74 and the electrodes 13 and 14 (FIGS. 1 and 2A-2F)or the electrodes 202 and 204 (FIG. 2G), into the malfunctioning heart in an effort to effect defibrillation, the energy level being higher than would have been the case had the capacitor been discharged three seconds earlier. The delay circuit may be composed of an RC circuit connected to the comparator 67 so that the capacitor thereof charges toward the ONE level slowly; for example the capacitor may take about three (3) seconds or more as indicated above to achieve the ONE level, allowing time to receive one or more synchronizing pulses from the pulse shaper 72, if present.

The sample-and-hold circuit 57 is reset whenever the comparator 61 output goes from ONE to ZERO, which occurs when the difference between the stored signal representing baseline mean pressure and the signal representing current mean pressure returns to an acceptable level, indicating that the hemodynamic compromise has been overcome. The resetting is accomplished by an inverter 77 and a differentiating circuit constituted by a capacitor 78 and a resistor 80 connected in series in the denominated order from the output terminal of the inverter 77 to ground, a positive going spike appearing across the resistor 80 each time the input to the inverter 77 from the comparator 61 goes from ONE to ZERO.

In the event the first pulse delivered to the heart fails to effect a correction in the pressure (which would cause the output of the comparators 54 and 61 to become ZERO, removing the enable signals from the sample-and-hold circuit 57 and the converter 63), the capacitor 65 is recharged and discharged a number of additional times, for example three more times in an effort to correct the malfunction. The number of discharges is sensed by a counter 81, which has its input connected to the output of the OR gate 73. If the counter 81 reaches a count of four within the given time period, for example a period of three minutes, its output goes from ZERO to ONE, which is applied to the converter 63 as a disabling (OFF) signal. An internal timer within the converter 63 holds the converter OFF for a given period so that the patient will not receive more shocks during this given period. At the end of the period the converter 63 returns to a READY condition and is again able to respond to an ENABLE signal from the comparator 61. The counter 81 resets itself to zero whenever it either reaches its maximum count of four or fails to reach the count of four within the given time period.

Figure 5A:
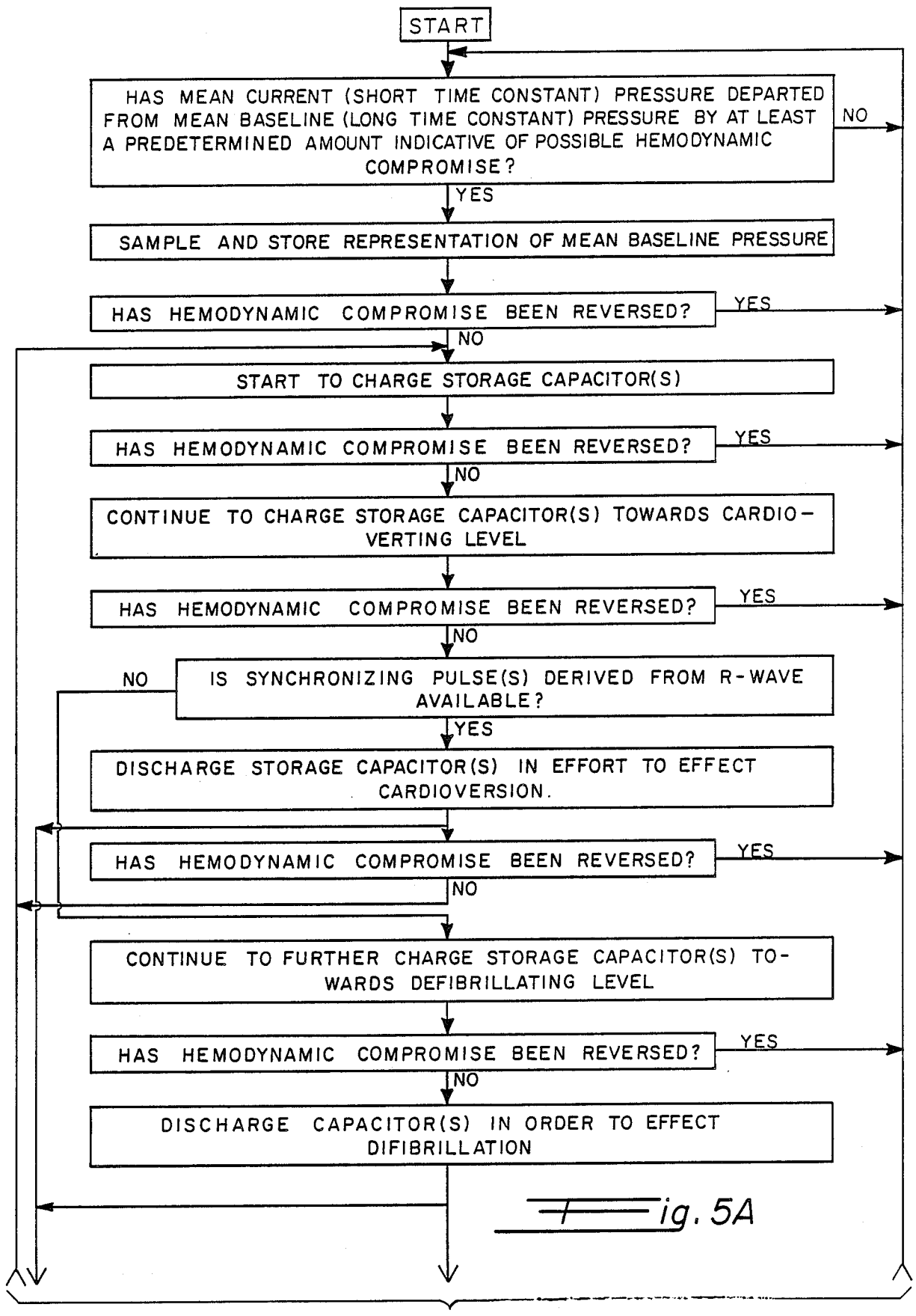
FIGS. 5A and 5B constitute a first exemplary flowchart of a series of actions or steps which may be carried out by the system of the present invention illustrated in FIG. 4 and effect achievement of the invention in its method aspect.
Figure 5B:
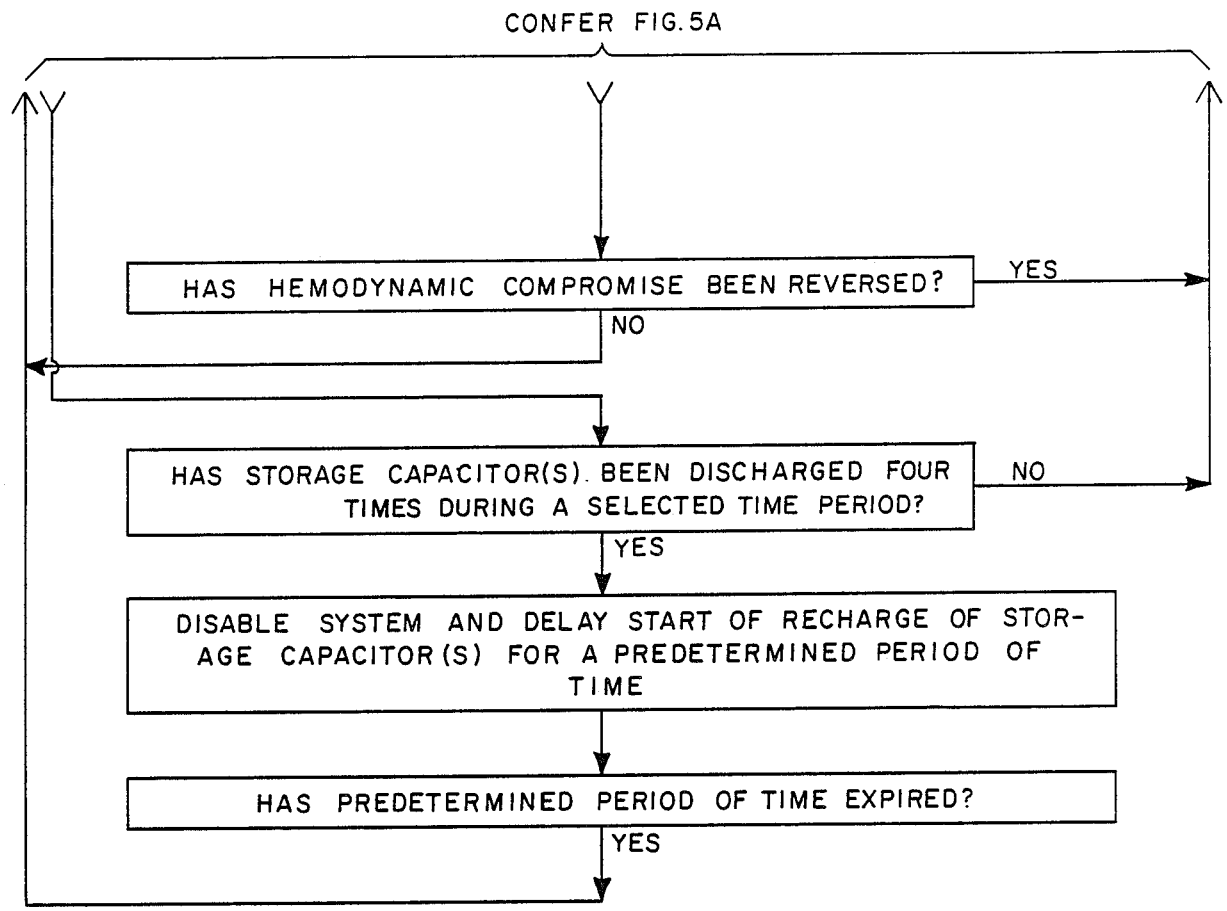

It is to be appreciated that the circuit described above may be considered, at least in part, to be a controller or processor, which could be realized as a microprocessor, the processor being identified by the numeral 82. The processor 82, with its associated components, in effect carries out the steps set out in the flowchart of FIGS. 5A and 5B.

The circuit of FIG. 4 could be associated with an antitachycardia pacemaker and/or an antibradycardia pacemaker, if desired.

Turning to FIG. 6, a second exemplary embodiment of the circuit components, which may be positioned within the housing 12 (FIGS. 1 and 3) or the apparatus 208 (FIG. 2G) includes a pair of input terminals 41, 42 which receive the variable D.C. voltage output signal representing pressure from the pressure responsive transducer 20 (FIGS. 1 and 2A–2F) or the noninvasive transducer (in system of FIG. 2G), the terminal 42 being connected to a point of circuit reference potential (ground). The terminals 41, 42 are connected to an amplifier 43, which amplifies the pressure representing D.C. input signal and feeds the same to respective buffer amplifiers 44 and 45. The circuit of FIG. 6, with associated components, is suitable for practicing the present invention in which both pressure and beating rate criteria are to be taken into account. The rate criterion is examined first and, if met, the pressure criteria are then considered.

The output from the buffer amplifier 45 is supplied to an RC circuit constituted by an adjustable resistor 46 connected to ground via a series connected storage capacitor 47 having a large adjustable resistor 48 connected in parallel therewith. The time constants (charging and discharging) of these circuit components are such that the D.C. voltage across the capacitor 47 represents the mean pressure sensed by the transducer 20 (FIGS. 1 and 2A–2F) or the noninvasive transducer (in system of FIG. 2G) over a relatively long period, for example during the preceding fifteen (15) minutes or even longer (for example a number of hours) or shorter (for example one hundred twenty (120) seconds) being suitable in some cases. The D.C. voltage level across the capacitor 47 thus represents a long term mean baseline pressure. The term "mean" as used herein is broad and includes the average value, as well as values near the average. The output from the buffer amplifier 44 is supplied to a second RC circuit constituted by an adjustable resistor 50 connected to ground via a capacitor 51, which has an adjustable resistor 52 connected in parallel therewith. The time constants (charging and discharging) of these circuit components are such that the D.C. voltage which appears across the capacitor 51 represents the short term mean pressure sensed by the transducer 20 (FIGS. 1 and 2A–2F) or the noninvasive transducer (in system of FIG. 2G) over a relatively short period, for example, during the preceding fifteen (15) seconds or longer (for example 60 seconds) or shorter (for example six seconds).

As illustrated the long term (baseline) and short term (current) D.C. voltage signals which appear across the respective capacitors 47 and 51 are fed respectively to the signal input terminal of a sample-and-hold circuit 57 and to the signal input terminal of a gate 56. A rate sensing-circuit 83 is arranged to receive a beating rate (R-wave) signal (first control signal) from the rate sensing electrodes 18a, 18b (FIGS. 1 and 2A–2F) or from the rate sensing electrodes 212, 213 (FIG. 2G). Whenever the rate exceeds a given rate, for example 155 beats per minute, indicating tachycardia, the output terminal of the rate sensing circuit 83 goes from low (ZERO) to high (ONE). The ONE signal is supplied as an enabling input to the gate 56 and to sample-and-hold circuit 57. The D.C. voltage representing current mean pressure appearing across the capacitor 51 is fed via the enabled gate 56 to the noninverting input terminal of an operational amplifier 60. The D.C. voltage representing mean baseline pressure appearing across the capacitor 47 is transferred to the sample-and-hold circuit 57, appearing across its associated capacitor 58. This stored D.C. voltage representing mean baseline pressure is supplied to the inverting input terminal of the operational amplifier 60 which has its noninverting input terminal connected to the output terminal of the gate 56 which, when enabled as noted above, passes the D.C. voltage signal appearing across the capacitor 51 and representing current mean pressure to the operational amplifier 60. As illustrated, the input terminals of the operational amplifier are connected as they would be to receive signals other than arterial pressure. Were MAP to be the selected hemodynamic parameter, the terminals would be reversed.

The output from the operational amplifier 60 is supplied to an input terminal of a comparator 61, which has its other input connected to the wiper of a potentiometer 62 connected between ground and the +15 volt power supply bus. Whenever the voltage supplied to the comparator 61 from the operational amplifier 60 exceeds the voltage supplied from the potentiometer 62, an indication of hemodynamic compromise, the output terminal of the comparator 61 goes from low (ZERO) to high (ONE) and the signal second control signal is passed to the enable terminal of a D.C.-to-D.C. converter 63. The D.C.-to-D.C. converter 63, when enabled, receives current from a low voltage battery pack or battery 64 and converts it into a high D.C. voltage, for example a voltage of 720 volts, which is used, when the converter is enabled, to charge an energy storage capacitor 65, via a resistor 66 towards the high voltage. The capacitor 65 is of such size that it will store energy levels sufficient to produce the desired cardioverting-/defibrillation pulses. The desired pulse for cardioversion is a truncated exponential pulse of about 25 Joules delivered approximately 17 seconds from onset of the hemodynamic compromise.

Once the capacitor 65 is charged to a sufficiently high D.C. voltage level to provide sufficient energy to effect cardioversion, as determined by a comparator 67, which receives on one input terminal a voltage proportional to the instant D.C. voltage across the capacitor 65, a resistive voltage divider 68 being in parallel to the capacitor 65. The second input terminal of the comparator 67 is connected to the wiper of a potentiometer 70 which is connected between ground and the +15 volt bus. When the voltage across the energy storing capacitor 65 is sufficient to supply a cardioverting energy pulse to the malfunctioning heart, the voltage supplied to the one input terminal of the comparator 67 exceeds the voltage supplied to its other input terminal from the potentiometer 70 via its associated wiper. Under these conditions, the output from the comparator 67 goes from low (ZERO) to high (ONE), which ONE signal effects an enabling of an analog gate 71. The gate 71 has its signal input connected to receive an output from a pulse shaper 72, which receives an input from the rate sensing electrodes 18a, 18b (FIGS. 1 and 2A-2F) or from the rate sensing electrodes 212, 213 (FIG. 2G) and produces a pulse train in synchronism with the R-wave supplied from the electrodes 18a, 18b or from the electrodes 212, 213. If the pulse train from the pulse shaper 72 is present, these pulses are passed, via the gate 71, to an OR circuit 73 and thence to the gate electrode of an SCR 74. The first of these pulses which, if present, appears on the gate electrode fires the SCR 74 thereby discharging the energy stored on the capacitor 65 into the malfunctioning heart, via the electrodes 13 and 14 (FIGS. 1 and 2A-2F) or the electrodes 202, 204 (FIG. 2G) in an effort to effect cardioversion, the discharge being affected in synchronism with the R-wave.

In the event that the pulse shaper 72 does not produce a pulse to fire the SCR 74 because of the absence of an R-wave, the ONE signal from the comparator 67 is passed, via a delay circuit 75, which provides a delay of about three seconds or more, and enables a pulse generator 76 causing it to produce output pulse to initiate defibrillation. The pulse is supplied, via the OR circuit 73, to the gate electrode of the SCR 74 causing the SCR to fire. The energy storage capacitor 65, which during the elapsed three seconds has charged to a higher level, discharges, via the SCR 74 and the electrodes 13 and 14 (FIGS. 1 and 2A-2F) or electrodes 202 and 204 (FIG. 2G), into the malfunctioning heart via the electrodes 13 and 14 (FIGS. 1 and 2A-2F) or electrodes 202 and 204 (FIG. 2G) in an effort to effect defibrillation, the energy level being higher than it would had been had discharge been effected three (3) or more seconds earlier. The delay circuit may be composed of an RC circuit connected to the comparator 67 so that the capacitor thereof charges toward the ONE level slowly; for example the capacitor may take about three (3) seconds or more to achieve the ONE level, allowing time to receive one or more synchronizing pulses from the pulse shaper 72, if present.

The sample-and-hold circuit 57 is reset whenever the comparator 61 output goes from ONE to ZERO, which occurs when the difference between the baseline mean pressure and current mean pressure returns to an acceptable noncompromising level. The resetting is accomplished by an inverter 77 and a differentiating circuit constituted by a capacitor 78 and a resistor 80 connected in series in the denominated order from the output terminal of the inverter 77 to ground, a positive going spike appearing across the resistor 80 each time the input to the inverter 77 from the comparator 61 goes from ONE to ZERO.

In the event the first pulse delivered to the heart fails to effect a correction in the pressure by overcoming the hemodynamic compromise (which would cause the output of the comparator 61 to become ZERO, removing the enable signal from the converter 63), the capacitor 65 is recharged and dscharged a number of additional times, for example three more times in an effort to correct the malfunction. The number of discharges is sensed by a counter 81, which has its input connected to the output of the OR gate 73. If the counter 81 reaches a count of four within the given time period, for example a period of three minutes, its output goes from ZERO to ONE, which is applied to the converter 63 as a disabling (OFF) signal. The counter 81 resets itself to ZERO count whenever it either reaches its maximum count of four or fails to reach the count of four within the given time period. An internal timer within the converter 63 holds the converter OFF for a given period so that the patient will not receive more shocks during this given period. At the end of the period the converter 63 returns to a READY condition and is again able to respond to an ENABLE signal from the comparator 61.

As can be seen from the foregoing description of the operation of the circuit of FIG. 6, cardioverting/defibrillating D.C. pulses are delivered to the malfunctioning heart only when the rate criterion is first satisfied and, thereafter, the pressure criteria also satisfied. This can be viewed as a series rate-pressure algorithm.

In the event the rate criterion is met, but the pressure criteria are not; that is to say no hemodynamic compromise presents, the circuit of FIG. 6 nevertheless acts to enable an antitachycardia pacemaker 86 which supplies pacing signals to the pair of pacing electrodes 21, 22 (FIGS. 1 and 2A-2F) or the pair of pacing electrodes 210, 211 (FIG. 2G). To enable the pacemaker 86, two signals must be supplied to an AND circuit 85, the first being a ONE signal from the rate sensing circuit 83, the second being a ONE signal supplied to the AND circuit 85 via an inverter 84 from the output terminal of the comparator 61. When no hemodynamic compromise prevails, the output terminal of the comparator 61 has a low (ZERO) output. This ZERO output is inverted by the inverter 84 and appears as a ONE on the second input terminal of the AND circuit 85. Thus, when both inputs to the AND circuit 85 are ONE, the antitachycardia pacemaker 86, which may be any one of a number of conventional types is energized.

Figure 7A:
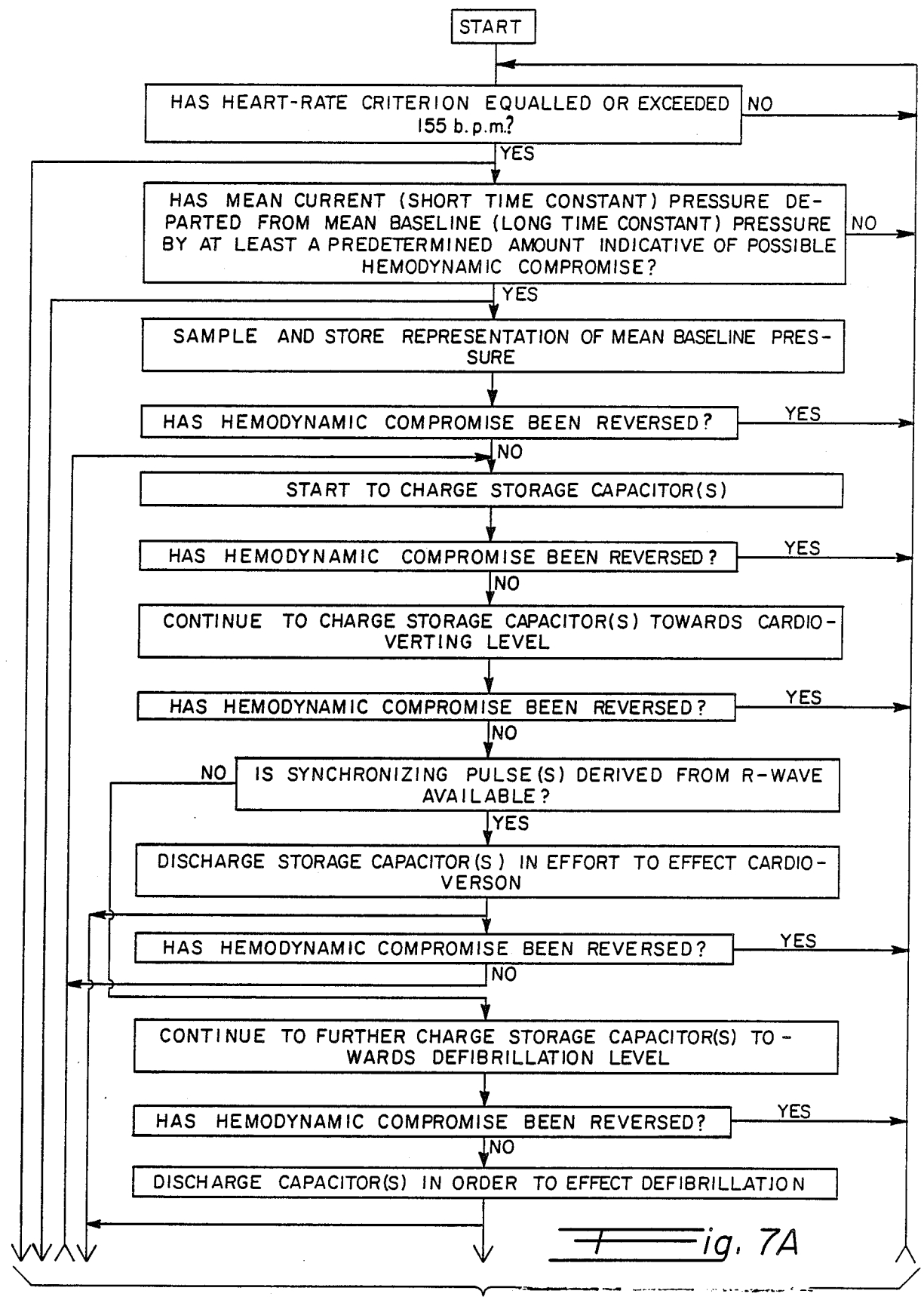
FIGS. 7A and 7B constitute a econd exemplary flowchart of a series of actions or steps which may be carried out by the system of the present invention illustrated in FIG. 6 and effect achievement of the invention in its method aspect.
Figure 7B:
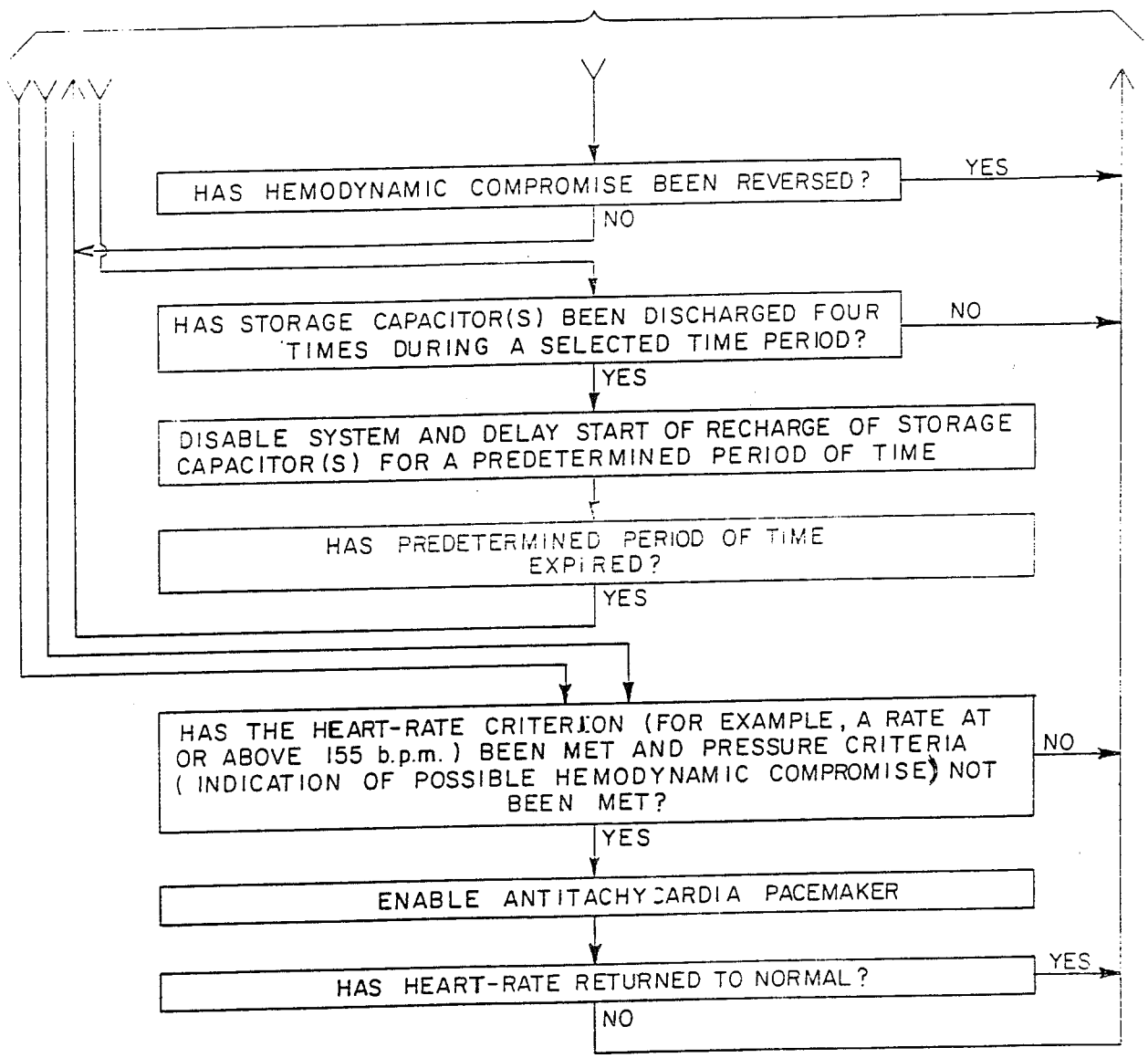
Figure 7B:
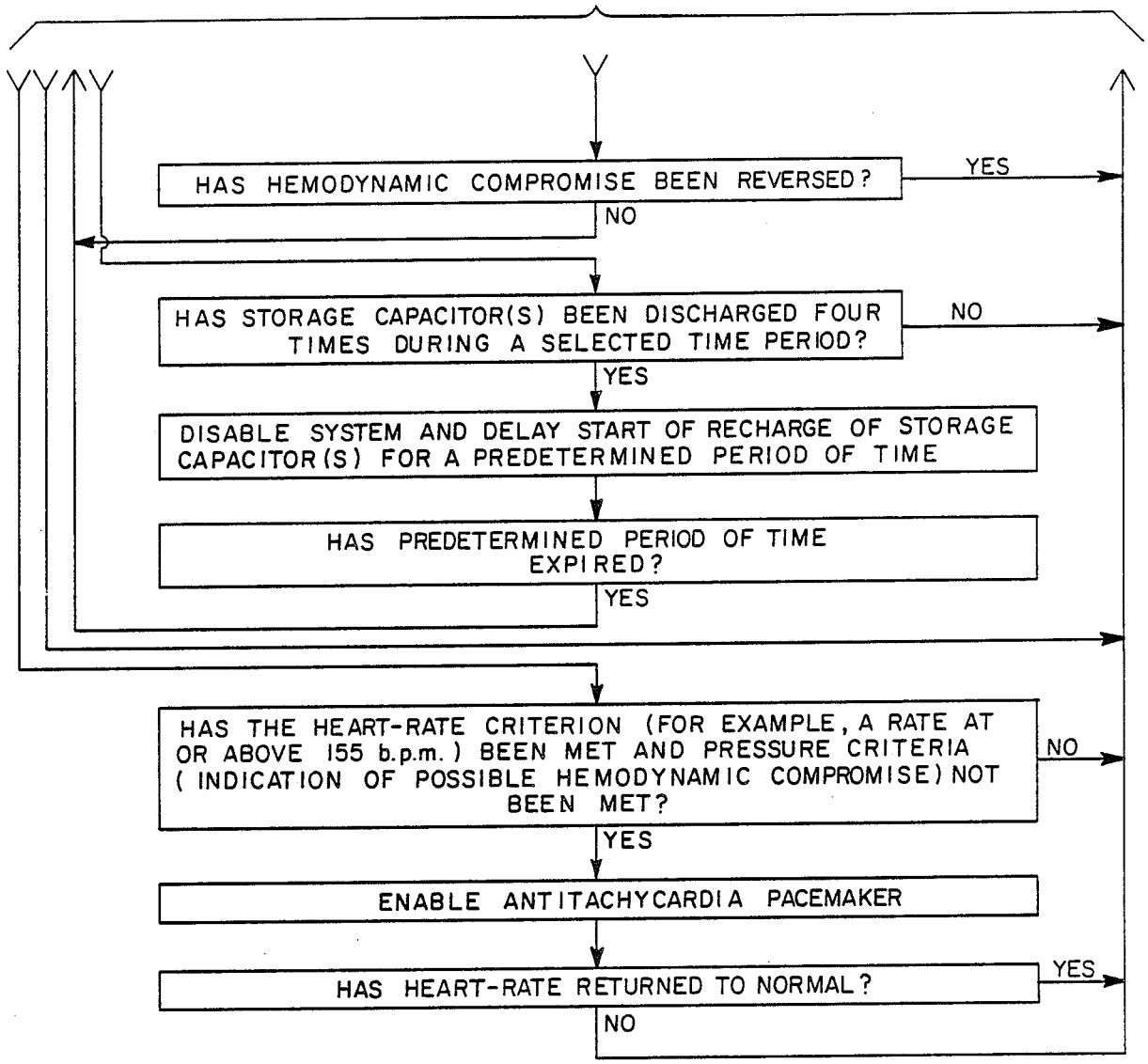

It is to be appreciated that the circuit described above may be considered, at least in part, to be a processor, which could be realized as a microprocessor, the processor being identified by the numeral 82. The processor 82, with its associated components, in effect carries out the steps set out in the flowchart of FIGS. 7A and 7B.

It is to be understood that the system of FIG. 6 could be associated with a failsafe antibradycardia pacing system, if desired.

Turning to FIG. 8, a third exemplary embodiment of the circuit components, which may be positioned within the housing 12 (FIGS. 1 and 3) or the apparatus 208 (FIG. 2G) includes a pair of input terminals 41, 42 which receive the variable D.C. voltage output signal representing pressure from the pressure responsive transducer 20 (FIGS. 1 and 2A-2F) or the noninvasive transducer (in system of FIG. 2G), the terminal 42 being connected to a point of circuit reference potential (ground). The terminals 41, 42 are connected to an amplifier 43, which amplifies the pressure representing D.C. input signal and feeds the same to respective buffer amplifiers 44 and 45. The circuit of FIG. 8 can be used in practicing the present invention using both rate and pressure criteria. In this case the rate and pressure criteria must exist simultaneously to start the sample-and-hold function.

The output from the buffer amplifier 45 is supplied to an RC circuit constituted by an adjustable resistor 46 connected to ground via a series connected capacitor 47 having a large adjustable resistor 48 connected in parallel therewith. The time constants (charging and discharging) of these circuit components are such that the D.C. voltage across the capacitor 47 represents the mean pressure sensed by the transducer 20 (FIGS. 1 and 2A-2F) or the noninvasive transducer (in system of FIG. 2G) over a relatively long period, for example during the preceding fifteen (15) minutes or even longer for example a number of hours) or shorter (for example one hundred twenty (120) seconds being suitable in some cases. The D.C. voltage level across the capacitor 47 thus represents a long term mean baseline pressure. The term "mean" as used herein is broad and includes the average value, as well as values near the average. The output from the buffer amplifier 44 is supplied to a second RC circuit constituted by an adjustable resistor 50 connected to ground via a capacitor 51, which has an adjustable resistor 52 connected in parallel therewith. The time constants (charging and discharging) of these circuit components are such that the D.C. voltage which appears across the capacitor 51 represents the short term mean pressure sensed by the transducer 20 (FIGS. 1 and 2A-2F) or the noninvasive transducer (in system of FIG. 2G) over a relatively short period, for example, during the preceding fifteen (15) seconds or longer (for example 60 seconds) or shorter (for example six seconds).

As illustrated the long term (baseline) and short term (current) D.C. voltage signals which appear across the respective capacitors 47 and 51 are fed respectively to the inverting and noninverting terminals of an operational amplifier 87, a difference D.C. voltage signal appearing as the output from the operational amplifier 87. As illustrated, the input terminals of the operational amplifier 87 are connected as they would be were pressure other than arterial pressure were involved. Were MAP to be the selected hemodynamic parameter, the terminals would be reversed. The D.C. output signal from the operational amplifier 87 is fed to a first input terminal of a comparator 88. The second input terminal of the comparator 88 is connected to the wiper of a potentiometer 89 which is connected between ground and a point of fixed D.C. potential, illustrated as being +15 volts, from an internal power supply bus.

Whenever the voltage supplied to the comparator 88 from the operational amplifier 87 exceeds the voltage supplied via the wiper from the potentiometer 89, a low (ZERO) level on the output terminal from the comparator 88 goes high (ONE), the ONE signal being coupled to a first input terminal of an AND circuit 90 which has its other input terminal coupled to the output terminal of a rate sensing circuit 83, which produces a ONE signal on its output terminal whenever the heart rate exceeds a predetermined value, for example 155 beats per minute. When the AND gate 90 receives ONE signals on both its input terminals, its output goes high (ONE) which enables a gate 56. The ONE signal from the AND gate 90 is also fed as an enabling input to a sample-and-hold circuit 57. The voltage representing current mean pressure appearing across the capacitor 51 is fed to the noninverting input terminal of an operational amplifier 60. The voltage representing mean baseline pressure appearing across the capacitor 47 is fed to the sample-and-hold circuit 57. Were MAP to be the selected hemodynamic parameter, the input terminals of the operational amplifier 60 would be reversed.

A D.C. output from the sample-and-hold circuit 57 is stored in a storage circuit, for the purpose of illustration shown as a capacitor 58. This stored voltage is supplied to the inverting input terminal of the operational amplifier 60 which has its noninverting input terminal connected to the output terminal of the gate 56, which when enabled, passes the D.C. voltage signal appearing across the capacitor 51 and representing current mean pressure to the operational amplifier 60. The output from the operational amplifier 60 is supplied to an input terminal of a comparator 61, which has its other input connected to the wiper of a potentiometer 62 connected between ground and the +15 volt power supply bus. Whenever the voltage supplied to the comparator 61 from the operational amplifier 60 exceeds the voltage supplied from the potentiometer 62, an indication of hemodynamic compromise, the output terminal of the comparator 61 goes from low (ZERO) to high (ONE) which signal is passed to the enable terminal of a D.C.-to-D.C. converter 63. It is to be appreciated that the wipers of the potentiometers 89 and 62 can be adjusted independently. Thus, one can set the wiper of the potentiometer 62 so that the hemodynamic compromise must get worse than it was when the sample-and-hold circuit 57 is enabled before the output from the comparator 61 enables the D.C.-to-D.C. converter 63. The D.C.-to-D.C. converter 63, when enabled, receives current from a low voltage battery pack or battery 64 and converts it into a high D.C. voltage, for example a voltage of 720 volts, which is used, when the converter is enabled, to charge an energy storage capacitor 65, via a resistor 66 towards the high voltage. The capacitor 65 is of such size that it will store energy levels sufficient to produce the desired cardioverting/defibrillation pulses. The desired pulse for effecting cardioversion is a truncated exponential pulse of about 25 Joules delivered approximately 17 seconds from onset of the hemodynamic compromise.

Once the capacitor 65 is charged to a sufficiently high D.C. voltage level, as determined by a comparator 67, which receives on one input terminal a voltage proportional to the D.C. voltage across the capacitor 65, a resistive voltage divider 68 being in parallel to the capacitor 65. The second input terminal of the comparator 67 is connected to the wiper of a potentiometer 70 which is connected between ground and the +15 volt bus. When the voltage across the energy storing capacitor 65 is sufficient to supply a cardioverting energy pulse to the malfunctioning heart, the voltage supplied to the one input terminal of the comparator 67 exceeds the voltage supplied to its other input terminal from the potentiometer 70 via its associated wiper. Under these conditions, the output from the comparator 67 goes from low (ZERO) to high (ONE), which ONE signal effects an enabling of an analog gate 71. The gate 71 has its signal input connected to receive an output from a pulse shaper 72, which receives an input from the rate sensing electrodes 18a, 18b (FIGS. 1 and 2A-2F) or the rate sensing electrodes 212, 213 (FIG. 2G) and produces a pulse train in synchronism with the R-wave supplied from the electrodes 18a, 18b or the electrodes 212, 213. If the pulse train from the pulse shaper 72 is present, these pulses are passed, via the gate 71, to an OR circuit 73 and thence to the gate electrode of an SCR 74. The first of these pulses which, if present, appears on the gate electrode fires the SCR 74 thereby discharging the energy stored on the capacitor 65 into the malfunctioning heart, via the electrodes 13 and 14 (FIGS. 1 and 2A-2F) or the electrodes 202 and 204 (FIG. 2G) in an effort to effect cardioversion, the discharge being affected in synchronism with the R-wave.

In the event that the pulse shaper 72 does not produce a pulse to fire the SCR 74 because of the absence of an R-wave, the ONE signal from the comparator 67 is passed, via a delay circuit 75, which provides a delay of about three seconds or more, and enables a pulse generator 76 causing it to produce an output pulse which is supplied, via the OR circuit 73, to the gate electrode of the SCR 74 causing the SCR to fire. The energy storage capacitor 65, which by then has been charged to a higher level, discharges, via the SCR 74 and the electrodes 13 and 14 (FIGS. 1 and 2A-2F) or the electrodes 202 and 204 (FIG. 2G), into the malfunctioning heart in an effort to effect defibrillation. The delay circuit 75 may be composed of an RC circuit connected to the comparator 67 so that the capacitor thereof charges toward the ONE level slowly; for example the capacitor may take about three (3) seconds or more to achieve the ONE level, allowing time to receive one or more synchronizing pulses from the pulse shaper 72, if present.

The sample-and-hold circuit 57 is reset whenever the comparator 61 output goes from ONE to ZERO, which occurs when the difference between the baseline mean pressure and current mean pressure returns to an acceptable noncompromising level. The resetting is accomplished by an inverter 77 and a differentiating circuit constituted by a capacitor 78 and a resistor 80 connected in series in the denominated order from the output terminal of the inverter 77 to ground, a positive going spike appearing across the resistor 80 each time the input to the inverter 77 from the comparator 61 goes from ONE to ZERO.

In the event the first pulse delivered to the heart fails to effect a correction in the pressure (which would cause the output of the comparator 61 to become ZERO, removing the enable signal from the converter 63), the capacitor 65 is recharged and discharged a number of additional times, for example three more times, in an effort to correct the malfunction. The number of discharges is sensed by a counter 81, which has its input connected to the output of the OR gate 73. If the counter 81 reaches a count of four within the given time period, for example a period of three minutes, its output goes from ZERO to ONE, which is applied to the converter 63 as a disabling (OFF) signal. The counter 81 resets itself to zero whenever either it reaches its maximum count of four or it fails to reach a count of four within the given time period. An internal timer within the converter 63 holds the converter OFF for a given period so that the patient will not receive more shocks during this given period. At the end of the period the converter 63 returns to a READY condition and is again able to respond to an ENABLE signal from the comparator 61.

As can be seen from the foregoing description of the operation of the circuit of FIG. 8, cardioverting-/defibrillating D.C. pulses are delivered to the malfunctioning heart only when the rate and the pressure criteria are simultaneously satisfied. This can be viewed as a parallel rate-pressure algorithm.

In the event the rate criterion is met, but the pressure criteria are not; that is to say no hemodynamic compromise presents, the circuit of FIG. 8 nevertheless acts to enable an antitachycardia pacemaker 86 which supplies pacing signals to the pair of pacing electrodes 21, 22 (FIGS. 1 and 2A-2F) or the pacing electrodes 210, 211 (FIG. 2G). To enable the pacemaker 86, two signals must be supplied to an AND circuit 85, the first being a ONE signal from the rate sensing circuit 83, the second being a ONE signal supplied to the AND circuit 85 via an inverter 84 from the output terminal of the comparator 61. When no hemodynamic compromise prevails, the output terminal of the comparator 61 has a low (ZERO) output. This ZERO output is inverted by the inverter 84 and appears as a ONE on the second input terminal of the AND circuit 85. Thus, when both inputs are ONE, the antitachycardia pacemaker 86 is energized.

Figure 9A:
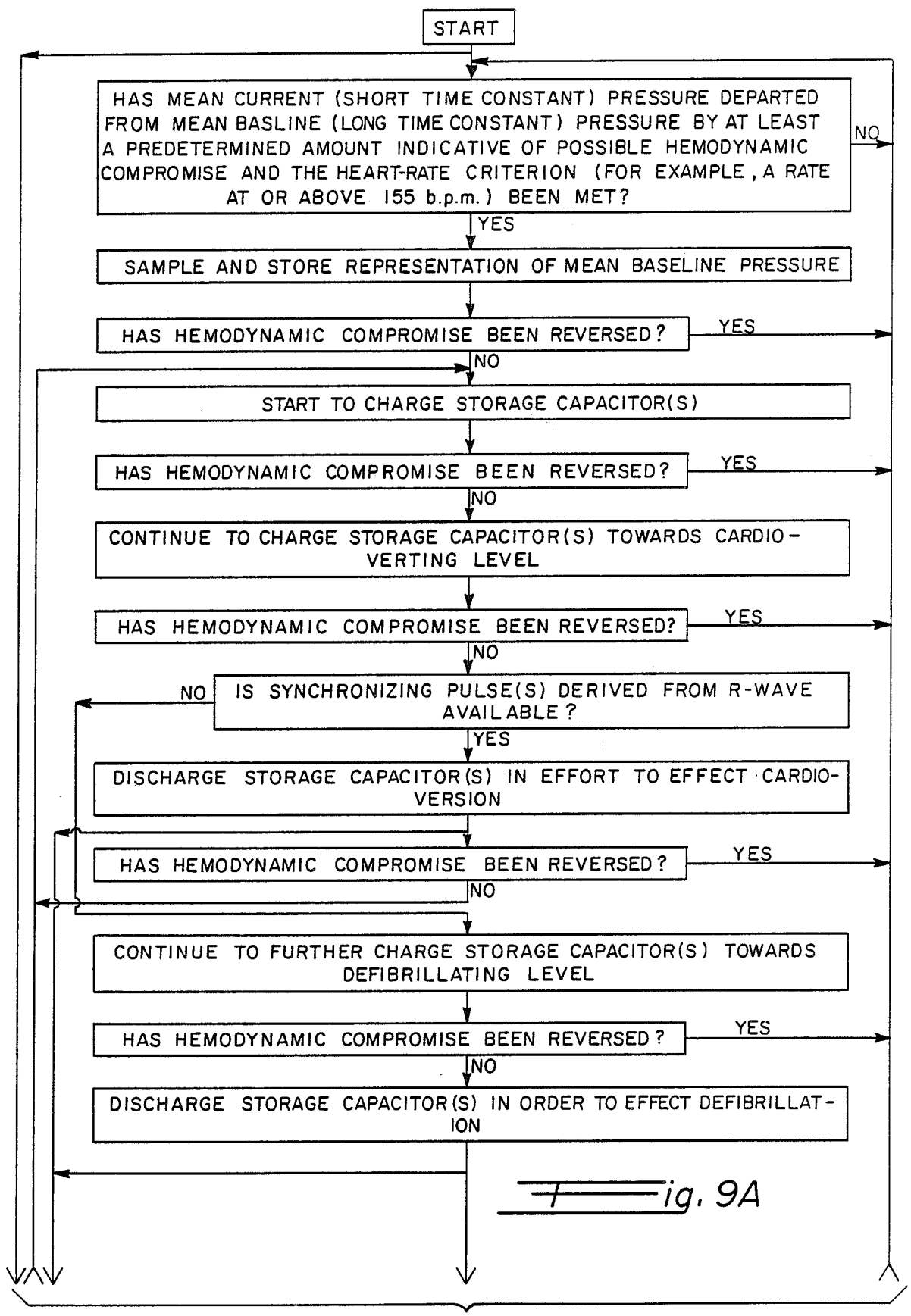
FIGS. 9A and 9B constitute a third exemplary flowchart of a series of actions or steps which may be carried out by the system of the present invention as illustrated in FIG. 8 and effect achievement of the invention in its method aspect.
Figure 9B:
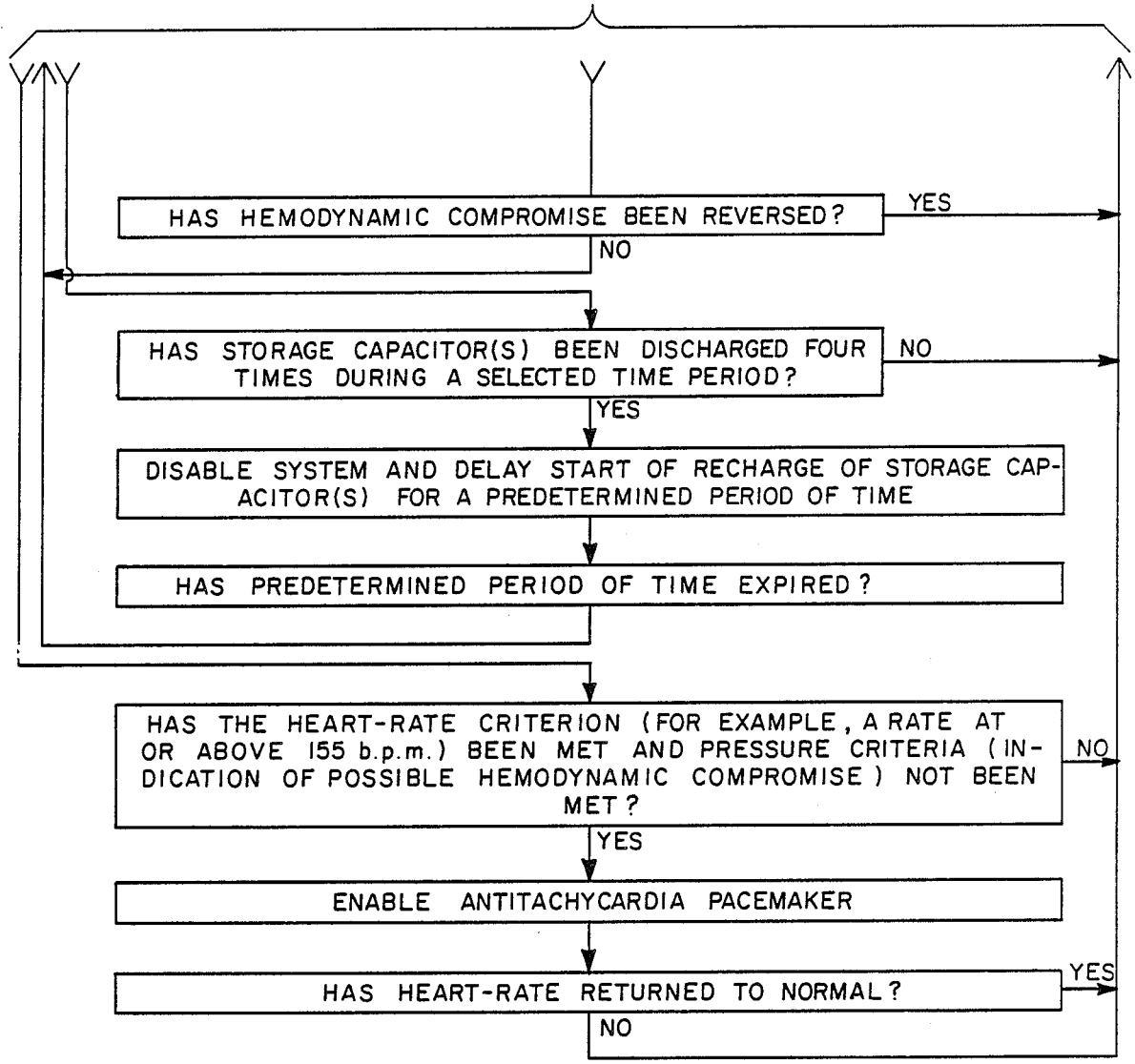
Figure 9B:
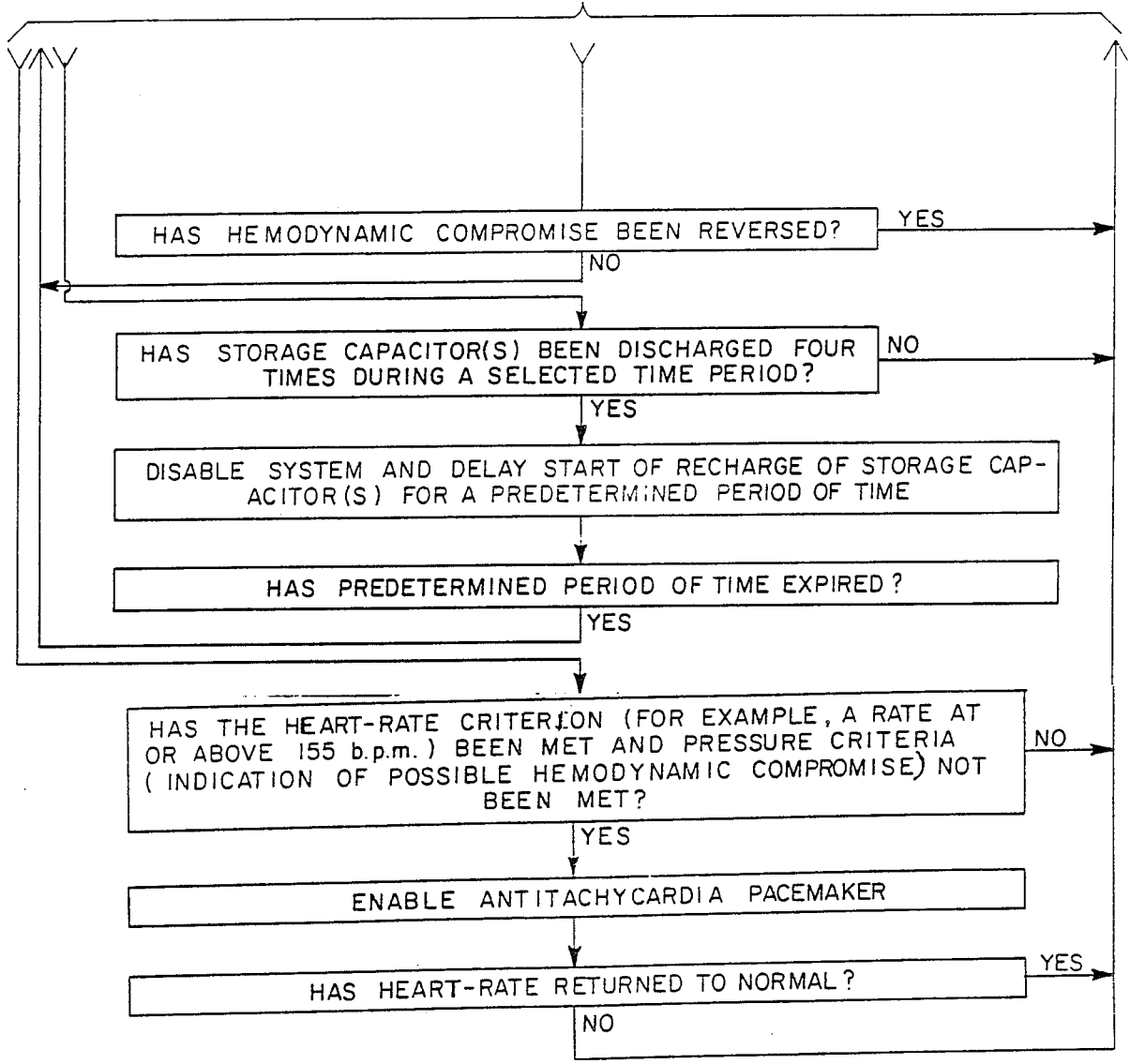
Figure 9A:
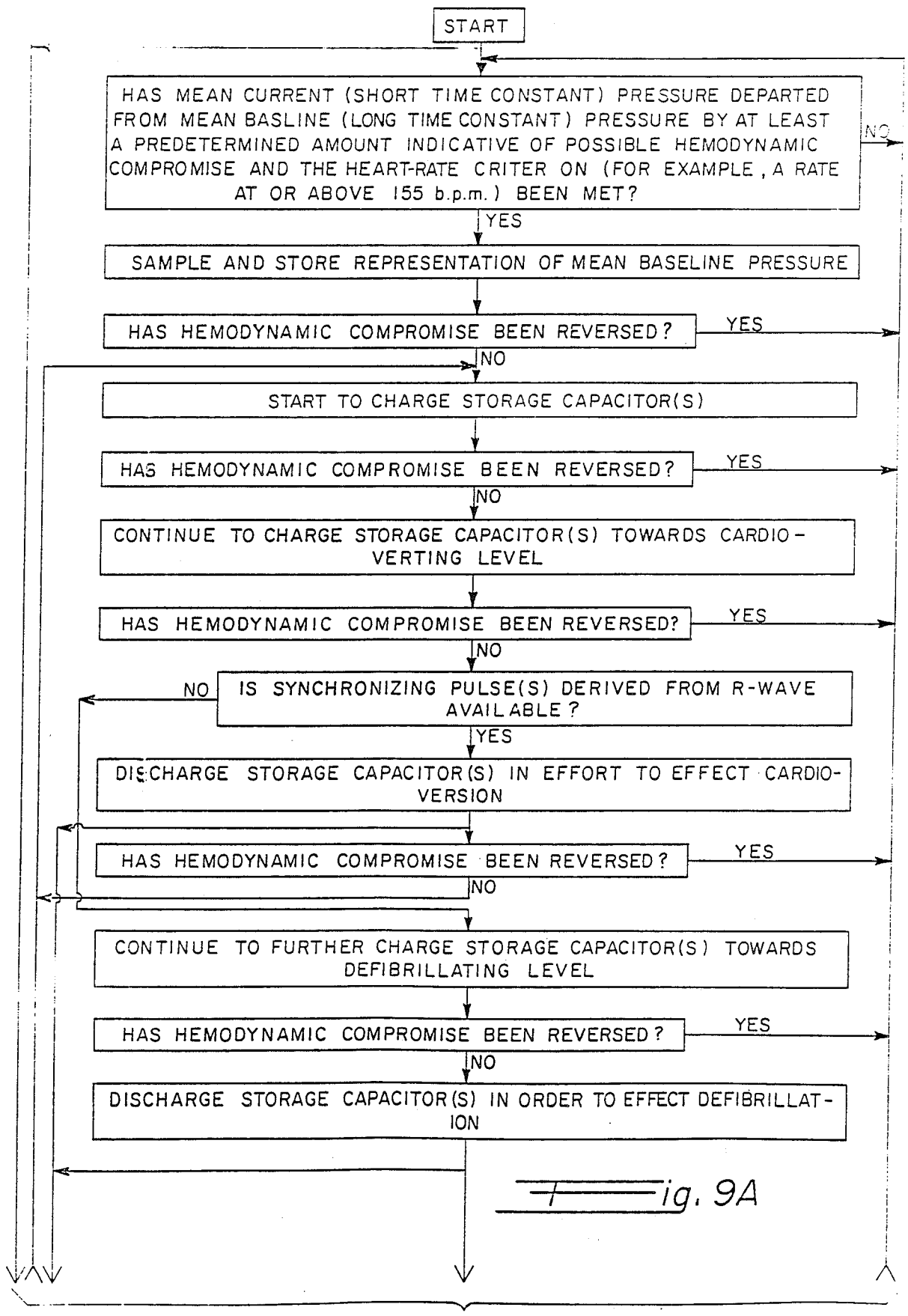

It is to be appreciated that the circuit described above may be considered, at least in part, to be a controller processor, which could be realized as a microprocessor, the processor being identified by the numeral 82. The processor 82, with its associated components, in effect carries out the steps set out in the flowchart of FIGS. 9A and 9B.

The circuit of FIG. 8 could be associated with a failsafe antibradycardia pacemaker, if desired.

Figure 10:
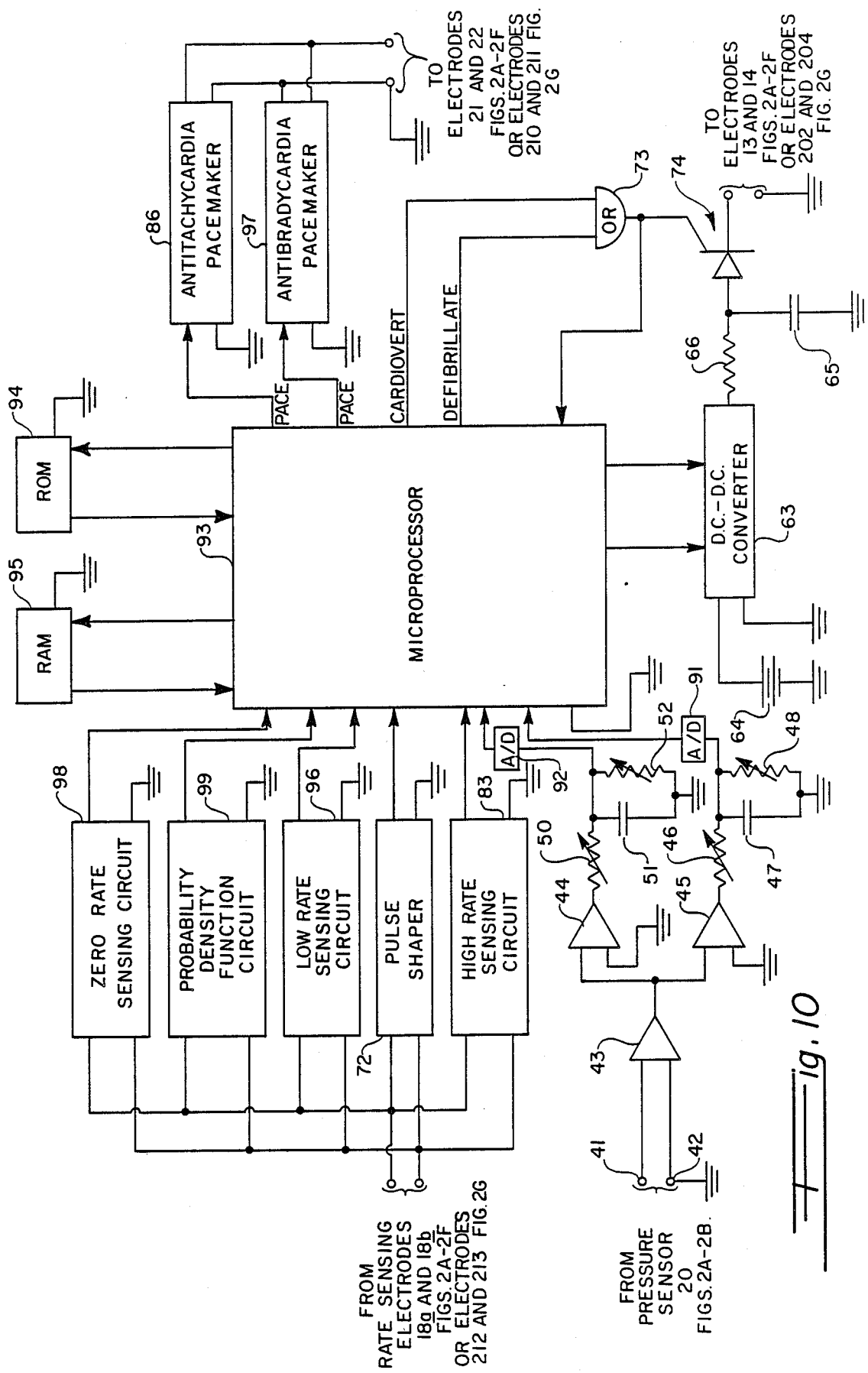
FIG. 10 is a partially block, schematic diagram of a hemodynamically responsive system for treating a malfunctioning heart which provides a microprocessor implementation in accordance with preferred embodiments of the present invention.

Turning to FIG. 10, a fourth exemplary embodiment of circuit components of a system for treating a malfunctioning heart, which may be positioned within the housing 12 (FIGS. 1 and 3) or in the apparatus 208 (FIG. 2G) or used in a portable system which may be carried on the body of a patient or used in fixed installation, such as in ICU's, CCU's, hospital rooms and the like includes a pair of input terminals 41, 42 which receive the variable D.C. voltage output signal representing pressure from the pressure responsive transducer 20 (FIGS. 1 and 2A-2F) or the noninvasive transducer (in system of FIG. 2G), the terminal 42 being connected to a point of circuit reference potential (ground). The terminals 41, 42 are connected to an amplifier 43, which amplifies the pressure representing D.C. input signal and feeds the same to respective buffer amplifiers 44 and 45. The circuit of FIG. 10 can be used in practicing the present invention using either pressure criterion alone or both rate and pressure criteria (either in parallel or series). The circuit of FIG. 10 can be used to carry out the methods, illustrated as algorithms in the flowcharts of FIGS. 5A, 5B and 7A, 7B and 9A, 9B, and can be considered as a digital, microprocessor-based version of the hand-wired analogue circuitry shown in FIGS. 4, 6 and 8. Of course, the microprocessor-based circuit of FIG. 10 could be programmed to carry out other routines. For example, were a rate criterion to be satisfied, the circuit could be arranged (1) simply to monitor pressure, (2) to effect antitachycardia pacing and/or to cardiovert. As further examples, were both rate and pressure criteria to be satisfied, the circuit of FIG. 10 could be programmed (1) to effect antitachycardia pacing and/or (2) to cardiovert/-defibrillate. Moreover, the selected interventions could be programmed so that when one is tried and fails, another is tried and so on. For example, if a tachycardia were detected regardless of whether or not hemodynamic compromise is present an antitachycardia pacemaker would attempt early to revert the arrhythms to normal and if this fails cardioversion/defibrillation would then attempt the same. A detailed discussion of one possible program is discussed below.

The output from the buffer amplifier 45 is supplied to an RC circuit constituted by an adjustable resistor 46 connected to ground via a series connected storage capacitor 47 having a large adjustable resistor 48 connected in parallel therewith. The time constants (charging and discharging) of these circuit components are such that the D.C. voltage across the capacitor 47 represents the mean pressure sensed by the transducer 20 (FIGS. 1 and 2A-2F) or the noninvasive transducer (in system of FIG. 2G) over a relatively long period, for example during the preceding fifteen (15) minutes or even longer (for example a number of hours) of shorter (for example 120 seconds) being suitable in some cases. The D.C. voltage level across the capacitor 47 thus represents a long term mean baseline pressure. The term "mean" as used herein is broad and includes the average value as well as values near the average. The output from the buffer amplifier 44 is supplied to a second RC circuit constituted by an adjustable resistor 50 connected to ground via a capacitor 51, which has an adjustable resistor 52 connected in parallel therewith. The time constants (charging and discharging) of these circuit components are such that the D.C. voltage which appears across the resistor 51 represents the short term mean pressure sensed by the transducer 20 (FIGS. 1 and 2A-2F) or the noninvasive transducer (in system of FIG. 2G) over a relatively short period, for example, during the preceding fifteen (15) seconds or longer (for example 60 seconds) or shorter (for example six seconds).

As illustrated the long term (baseline) and short term (current) D.C. voltage signals which appear across the respective capacitors 47 and 51 are fed respectively via respective analogue-to-digital converters (A/D's) 91 and 92 to respective inputs of a microprocessor 93. The A/D converters 91 and 92, in operation, convert the respective analogue signals which appear across capacitors 47 and 51 into corresponding digital signals for processing by the microprocessor 93, the microprocessor having associated therewith a ROM 94, which supplies programmed instructions to the microprocessor, and a RAM 95, which stores and supplies digital signal representations of pressure-related signals from and to the microprocessor.

Another input of the microprocessor 93 is supplied with high (ONE) and low (ZERO) signals from a high rate sensing circuit 83, which produces a ONE signal whenever the heart rate, as sensed by the electrodes 18a and 18b (FIGS. 2A-2F) or by the electrodes 212 and 213 (FIG. 2G), exceeds a predetermined rate, for example a rate of 155 b.p.m. The actual rate selected would, of course, depend on the individual patient and a professional opinion as to his or her condition. A pulse shaper 72, which also receives an input from the rate sensing electrodes 18a and 18b (FIGS. 2A-2F) or from the rate sensing electrodes 212 and 213 (FIG. 2G), is provided to supply narrow D.C. pulses to the microprocessor 93; if present, these pulses would be used as synchronizing pulses for cardioversion.

An antitachycardia pacemaker 86 is connected to an output terminal of the microprocessor 93 to receive therefrom a pace enable signal to, in effect, enable or turn on the pacemaker 86 under the command of the microprocessor 93. Two other output terminals from the microprocessor 93 provide respective cardiovert and defibrillate command signals to an OR circuit 73, which cooperates with a D.C.-to-D.C. converter 63, a battery 64, a charging resistor 66, storage capacitor 65 and a SCR 74 in the same manner as the corresponding circuit components having the same reference numerals function in the hand-wired circuits illustrated in FIGS. 4, 6 and 8. The output of the OR gate 73 is also supplied to an input terminal of the microprocessor 93, supplying signals to a counting means within the microprocessor 93 which corresponds to the counter 81 (FIGS. 4, 6 and 8).

As thus far described, the circuit of FIG. 10 can carry out the methods defined in the flowcharts of FIGS. 5A, 5B, and 7A, 7B and 9A, 9B, the respective programs being supplied by the ROM 94. In operation, the circuit of FIG. 10 can be seen as a microprocessor realization of the hand-wired analogue circuits of FIGS. 4, 6 and 8. It is to be appreciated that the circuit of FIG. 10 can be programmed to effect somewhat different routines and be provided with additional inputs, as well.

If desired for example, a low rate sensing circuit 96 could be provided, its input being coupled to the rate sensing electrodes 18a and 18b (FIGS. 2A-2F) or the rate sensing electrodes 212 and 213 (FIG. 2G). The low rate sensing circuit 96 supplies a high (ONE) signal to an input terminal whenever the beating rate, as sensed by the electrodes 18a and 18b or the electrodes 212 and 213, falls below a given rate, for example 45 b.p.m., indicative of bradycardia. Under these conditions (provided the rate were not zero), the microprocessor 93 would provide a command enable signal to an antibradycardia pacemaker 97. When enabled, the pacemaker 97 would supply bradycardiacorrecting pacing signals to a patient's heart via the pacing electrodes 21 and 22 (FIGS. 1 and 2A-2F) or the pacing electrodes 210 and 211 (FIG. 2G).

If desired, a zero rate sensing circuit 98, responsive to output from the rate sensing electrodes 18a and 18b (FIGS. 2A-2F) or the rate sensing electrodes 212 and 213 (FIG. 2G) can be provided. This zero rate sensing circuit 98 produces a high (ONE) output signal whenever the beating rate is zero, indicating the heart has stopped beating (sometimes referred to as going "flat line"). This may represent either asystole or fine ventricular fibrillation. Under this condition, the microprocessor 93 is programmed to first effect a charging and discharging of the storage capacitor 65, supplying a ONE signal via its command defibrillate output connection to the OR gate 73 and then to effect antibrachycardia pacemaking after a given number of capacitor(s) discharges (say 4) if no hemodynamic improvement is noted. The order of defibrillation and pacemaking may be programmed in a reverse manner as desired.

The circuit of FIG. 10 includes, if desired, a narrow window probability density function circuit 99, which has its input coupled to the sensing electrodes 18a and 18b or sensing electrodes 212 and 213. The probability density function circuit may be of the type disclosed in U.S. Pat. Nos. 4,184,493, 4,202,340 and 4,475,551 of Langer et al. and which produce a high (ONE) output signal whenever fine ventricular fibrillation is present. This ONE output is supplied to an input of the microprocessor 93 which, in accordance with its program stored in the ROM 94, effects the charging and discharging of the storage capacitor 65, supplying via its command defibrillate output a ONE signal to the OR gate 73 to initiate discharge.

Conventional antitachycardia systems function primarily as rate-only sensing devices and perform inadequately in differentiating hemodynamically stable from unstable tachycardias. Consequently, in the course of developing the present invention, mean right atrial (MRAP), mean right ventricular (MRVP), and mean arterial pressures (MAP) were studied by the applicant for determining if a basis was present to distinguish significant arrhythmias and serve as a basis for improving antitachycardia systems.

Hemodynamic responses to rapid atrial and ventricular pacing were examined in 10 closed-chest anesthetized dogs. Pressure monitoring catheters placed in the femoral artery, high right atrium (HRA), and right ventricular apex (RVA) measured MAP, MRAP, and MRVP at baseline heart rates and after 30 and 60 sec. rapid HRA and RVA pacing. Pressures recorded during rapid pacing (average of the pressures at 30 and 60 sec. of pacing) at pacing rates of 180, 250, and 280/min. were compared to those recorded initially at baseline heart rates.

An exemplary graphical representation of the ECG wave MAP and MRAP of one dog is illustrated in FIG. 11 along a time base of 15 seconds, the pacing rate in this case being 250 b.p.m. starting at time zero. The traces of MAP and MRAP indicate that the changes are slight; hemodynamic compromise is not indicated. As illustrated in FIG. 12, when the dog was subjected to a pacing rate of 280 b.p.m. starting at time zero, in this case as clearly shown by the traces, the MAP dropped markedly within two seconds and MRAP increased markedly within one second. Hemodynamic compromise prevailed. Thus, it is clear that the selected criteria can be sensed and properly form the basis of improved antitachycardia systems and methods. In FIG. 13, traces of MAP and MRAP of a dog whose heart has been placed in ventricular fibrillation at time zero clearly shows marked hemodynamic compromise, the traces of the MAP and MRAP indicating that MAP dropped and continued to drop to an extremely low level in about eight seconds, while the MRAP increased considerably within the same period. As sensing algorithms, a MRAP algorithm and a combined MRAP-rate algorithm were tested in this dog using a hand operated antitachycardia-defibrillator system. In FIG. 14, the ECG, MAP and MRAP traces of a dog whose heart was placed into ventricular fibrillation at time zero is shown for a time period of about 36 seconds, a defibrillating pulse having been applied after a time lapse of about 22 seconds. As shown in the MAP and MRAP traces of FIG. 14, considerable hemodynamics comprise appears from the onset of fibrillation and once the defibrillating pulse has been applied, is reversed. Moreover, normal beating rate was restored within about three seconds.

Rapid RVA pacing, simulating ventricular tachycardia, resulted in significant increases in MRAP ($5.5 \pm 0.5$ to $12.0 \pm 1.0$ mmHg., $p<0.001$) and MRVP ($11.0 \pm 1.2$ to $16.0 \pm 0.9$ mmHg., $p<0.02$) with marked hemodynamic compromise (MAP decreased from $85 \pm 6$ to $50 \pm 6$ mmHg., $p<0.01$). These parameters remained stable during HRA pacing (simulating atrial tachycardia). The sensing algorithms successfully indicated those arrhythmias requiring termination, hemodynamically unstable ventricular tachycardia and fibrillation. Hemodynamically stable tachycardias were merely monitored, not manually terminated.

Thus, one can conclude that MRAP, MRVP and MAP, as well as other mean pressures, are useful in distinguishing hemodynamically significant tachycardias and could be used a sensed parameters in hemodynamically responsive antitachycardia systems.

The present invention provides significant advancements in the treatment of patients having malfunctioning hearts. The systems of the present invention operate automatically. The baseline pressure and permitted deviations therefrom are not based on an average of a large sampled population or standard; rather, these parameters are patient-specific. Moreover, the baseline changes automatically in accordance with the activity level of the individual patient, his or her position (erect or sublime) his or her state (asleep or awake). Furthermore, the selected baseline data is stored, once a malfunction has been sensed, so that subsequent interventions during an episode of malfunction do not distort the patient-specific baseline.

It is to be understood that the foregoing detailed description and accompanying illustrations have been set out by way of example, not by way of limitation. Numerous other embodiments and variants are possible, without departing from the spirit and scope of the invention, its scope being defined in the appended claims.

What is claimed is:

1. A system for treating a malfunctioning heart, the system including storage means for storing electrical energy, electrode means for electrically coupling the storage means to the heart, pressure responsive sensing means for sensing pressure at a site in a circulatory system, means responsive to output from said sensing means for developing a variable first signal representing mean baseline pressure over a period of predetermined length, means responsive to output from said means for developing a second signal representing mean current pressure over a period of given length of lesser duration than the predetermined period, and means responsive to output from the means for developing the variable first signal and the second signal for charging and enabling discharge of the electrical energy stored by said storage means across said electrode means and into the heart upon change in mean current pressure of at least a predetermined amount from the mean baseline pressure.

2. The system of claim 1, wherein said pressure responsive sensing means for sensing pressure at a site in a circulatory system comprises means for sensing right atrial pressure.

3. The system of claim 2, including means responsive to the variable first signal and to the second signal for providing a control signal indicative of mean current right atrial pressure increasing by at least a predetermined amount from mean baseline right atrial pressure, and wherein said means for charging and enabling discharge is responsive to the control signal.

4. The system of claim 1, wherein said pressure responsive sensing means for sensing pressure at a site in a circulatory system comprises means for sensing right ventricular pressure.

5. The system of claim 4, including means responsive to the variable first signal and to the second signal for providing a control signal indicative of mean left ventricular pressure increasing by at least a predetermined amount from mean baseline right ventricular pressure, and wherein said means for charging and enabling discharge is responsive to the control signal.

6. The system of claim 1, wherein said pressure responsive sensing means for sensing pressure at a site in a circulatory system comprises means for sensing central venous pressure.

7. The system of claim 6, including means responsive to the first signal and to the second signal for providing a control output signal indicative of mean central venous pressure increasing by at least a predetermined amount from mean baseline central venous pressure, and wherein said means for charging and enabling discharge is responsive to the control signal.

8. The system of claim 1, wherein said pressure responsive sensing means for sensing pressure at a site in a circulatory system comprises means for sensing left atrial pressure.

9. The system of claim 8, including means responsive to the first signal and to the second signal for providing a control signal indicative of mean left atrial pressure increasing by at least a predetermined amount from mean baseline left atrial pressure, and wherein said means for charging and enabling discharge is responsive to the control signal.

10. The system of claim 1, wherein said pressure responsive sensing means for sensing pressure at a site in a circulatory system comprises means for sensing left ventricular pressure.

11. The system of claim 10, including means responsive to the first signal and to the second signal for providing a control signal indicative of mean left ventricular pressure increasing by at least a predetermined amount from mean baseline left ventricular pressure, and wherein said means for charging and enabling discharge is responsive to the control signal.

12. The system of claim 1, wherein said pressure responsive sensing means for sensing pressure at a site in a circulatory system comprises means for sensing arterial pressure.

13. The system of claim 12, including means responsive to the first signal and to the second signal for providing a control signal indicative of mean arterial pressure dropping by at least a predetermined amount from mean baseline arterial pressure, and wherein said means for charging and enabling discharge is responsive to the control signal.

14. The system of claim 1, including microprocessor means for developing a control signal to control the means for charging and enabling discharge of the electrical energy stored by the storage means.

15. The system of claim 1, including means responsive to the variable first signal and to the second signal for providing a control signal to control the means for charging and enabling discharge of the electrical energy stored by the storage means, the control signal being indicative of mean blood pressure at the site departing from mean baseline pressure at the site by at least a predetermined amount.

16. A system for treating a malfunctioning heart, the system comprising electrical means for sensing heart rate and producing a first control signal upon the heart rate exceeding a predetermined rate; pressure responsive sensing means for sensing pressure at a site in a circulatory system, means responsive to output from said pressure responsive sensing means for developing a first pressure-related signal representing mean baseline pressure over a period of predetermined length, means responsive to output from said sensing means for developing a second pressure-related signal representing mean current pressure over a period of given length of lesser duration than the period of predetermined length of producing a second control signal indicative of the mean current pressure departing from mean baseline pressure by at least a predetermined amount; controllable antitachycardia pacemaking means for supplying pacing signals to the heart; controllable cardioverting-/defibrillating means including storage means for storing electrical energy and electrode means for applying electrical energy from the storage means to the heart to cardiovert or to defibrillate same; control circuit means responsive to the first control signal and to the second control signal for enabling said antitachycardia pacemeaking means in response to presence of the first control signal and contemporaneous absence of the second control signal and for enabling said cardioverting/defibrillating means in response to contemporaneous presence of both the first control signal and the second control signal; and means for discharging electrical energy stored by said storage means across said electrode means and into the heart.

17. The system according to claim 16, including means responsive to output from said electrical means for sensing heart rate for developing a discharge-synchronizing signal synchronized to an R-wave, and wherein said means for discharging electrical energy across said electrode means and into the heart includes means for synchronizing the discharge with the discharge-synchronizing signal to effect cardioversion.

18. The system according to claim 17, wherein said means for discharging electrical energy across said electrode means and into the heart effects discharge on a nonsynchronized basis, in the absence of the synchronization signal, to effect defibrillation.

19. The system according to claim 16, wherein said means for discharging electrical energy across said electrodes and into the heart effects discharge on a nonsynchronized basis to effect defibrillation.

20. The system of claim 16, wherein said pressure responsive sensing means for sensing pressure at a site in a circulatory system comprises means for sensing right atrial pressure.

21. The system of claim 20, including means responsive to the first pressure-related signal and to the second pressure-related signal for providing the second control signal indicative of mean right atrial pressure increasing by at least a predetermined amount from mean baseline right atrial pressure.

22. The system of claim 16, wherein said pressure responsive sensing means for sensing pressure at a site in a circulatory system comprises means for sensing right ventricular pressure.

23. The system of claim 22, including means responsive to the first pressure-related signal and to the second pressure-related signal for providing the second control signal indicative of mean right ventricular pressure increasing by at least a predetermined amount from mean baseline right ventricular pressure.

24. The system of claim 16, wherein said pressure responsive sensing means for sensing pressure at a site in a circulatory system comprises means for sensing central venous pressure.

25. The system of claim 24, including means responsive to the first pressure-related signal and to second pressure-related signal for providing the second control output signal indicative of mean central venous pressure increasing at least a predetermined amount from mean baseline central venous pressure.

26. The system of claim 16, wherein said pressure responsive sensing means for sensing pressure at a site in a circulatory system comprises means for sensing left atrial pressure.

27. The system of claim 26, including means responsive to the first pressure-related signal and to the second pressure-related signal for providing the second control signal indicative of mean left atrial pressure increasing by at least a predetermined amount from mean baseline left atrial pressure.

28. The system of claim 16, wherein said pressure responsive sensing means for sensing pressure at a site in a circulatory system comprises means for sensing left ventricular pressure.

29. The system of claim 28, including means responsive to the first pressure-related signal and to the second pressure-related signal for providing the second control signal indicative of mean left ventricular pressure increasing by at least a predetermined amount from mean baseline left ventricular pressure.

30. The system of claim 16, wherein said pressure responsive sensing means for sensing pressure at a site in a circulatory system comprises means for sensing arterial pressure.

31. The system of claim 30, including means responsive to the first pressure-related signal and to the second pressure-related signal for providing the second control signal indicative of mean arterial pressure reaching a predetermined level below mean baseline arterial pressure, the second control signal indicating hemodynamic comprise.

32. In a method of treating a malfunctioning heart, the method including the step of sensing pressure at a site in a circulatory system, an improvement comprising determining variable mean baseline pressure from the sensed pressure over a period of predetermined length, determining mean current pressure from the sensed pressure over a period of given length of lesser duration than the predetermined period, and delivering cardioverting/defibrillating electrical energy to the heart in response to change of at least a predetermined magnitude in the mean current pressure from the mean baseline pressure.

33. The method of claim 32, wherein the step of sensing pressure at a site in a circulatory system comprises sensing right atrial pressure, and the method includes sensing heart rate, said step of delivering cardioverting/defibrillating electrical energy being taken upon the heart rate exceeding a given rate and current mean right atrial pressure exceeding variable mean baseline right atrial pressure by at least the predetermined magnitude.

34. The method of claim 32, wherein the step of sensing pressure at a site in a circulatory system comprises sensing right ventricular pressure, and the method includes sensing heart rate, said step of delivering cardioverting/defibrillating electrical energy being taken upon the heart rate exceeding a given rate and current mean right ventricular pressure exceeding variable mean baseline right ventricle pressure by at least the predetermined magnitude.

35. The method of claim 32, wherein the step of sensing pressure at a site in a circulatory system comprises sensing central venous pressure, and the method includes sensing heart rate, said step of delivering cardioverting/defibrillating electrical energy being taken upon the heart rate exceeding a given rate and current mean central venous pressure exceeding variable mean baseline central venous pressure by at least the predetermined magnitude.

36. The method of claim 32, wherein the step of sensing pressure at a site in a circulatory system comprises sensing left atrial pressure, and the method includes sensing heart rate, said step of delivering cardioverting/defibrillating electrical energy being taken upon the heart rate exceeding a given rate and current mean left atrial pressure exceeding variable mean baseline left atrial pressure by at least the predetermined magnitude.

37. The method of claim 32, wherein the step of sensing pressure at a site in a circulatory system comprises sensing left ventricular pressure, and the method includes sensing heart rate, said step of delivering cardioverting/defibrillating electrical energy being taken upon the heart rate exceeding a given rate and the current mean left ventricular pressure exceeding variable mean baseline left ventricular pressure by at least the predetermined magnitude.

38. The method of claim 32, wherein the step of sensing pressure at a site in a circulatory system comprises sensing arterial pressure, and the method includes sensing heart rate, said step of delivering cardioverting/defibrillating electrical energy being taken upon the heart rate exceeding a given rate and mean current arterial pressure departing from the variable mean baseline arterial pressure by at least the predetermined magnitude in a decreasing direction.

39. The method of claim 32, wherein the step of sensing pressure at a site in a circulatory system comprises sensing right atrial pressure, said step of delivering cardioverting/defibrillating electrical energy being taken upon mean current right atrial pressure exceeding baseline right atrial pressure by at least the predetermined magnitude.

40. The method of claim 32, wherein the step of sensing pressure at a point in a circulatory system comprises sensing right ventricular pressure, said step of delivering cardioverting/defibrillating electrical energy being taken upon mean current right ventricular pressure exceeding mean baseline right ventricular pressure by at least the predetermined magnitude.

41. The method of claim 32, wherein the step of sensing pressure at a point in a circulatory system comprises sensing central venous pressure, said step of delivering cardioverting/defibrillating electrical energy being taken upon mean current central venous pressure exceeding mean baseline central venous pressure by at least the predetermined magnitude.

42. The method of claim 32, wherein the step of sensing pressure at a point in a circulatory system comprises sensing left atrial pressure, said step of delivering cardioverting/defibrillating electrical energy being taken upon mean current left atrial pressure exceeding mean baseline left atrial pressure by at least the predetermined magnitude.

43. The method of claim 32, wherein the step of sensing pressure at a point in a circulatory system comprises sensing left ventricular pressure, said step of delivering cardioverting/defibrillating electrical energy being taken upon mean current left ventricular pressure exceeding mean baseline left ventricular pressure by at least the predetermined magnitude.

44. The method of claim 32, wherein the step of sensing pressure at a point in a circulatory system comprises sensing arterial pressure, said step of cardioverting/defibrillating electrical energy being taken upon mean current arterial pressure departing from mean baseline arterial pressure by at least the predetermined magnitude in a decreasing direction.

45. A system for treating a malfunctioning heart, the system including means for providing cardioverting/defibrillating electrical energy, pressure responsive sensing means for sensing pressure at a site in a circulatory system, means responsive to output from said pressure responsive sensing means for developing a variable signal representing mean pressure over a period of predetermined length, means responsive to output from said pressure responsive sensing means for developing a further signal representing mean pressure over a period of given length of lesser duration than the period of predetermined length, and means responsive to the variable signal and to the further signal for delivering the cardioverting/defibrillating electrical energy into the heart upon occurrence of departure of the further signal from the variable signal by at least a predetermined magnitude indicative of hemodynamic comprise.

46. A system for treating a malfunctioning heart, the system comprising electrical means for sensing heart rate and producing a first control signal whenever the rate exceeds a predetermined rate, pressure responsive means for sensing pressure at a site in a circulatory system; means responsive to output from the pressure responsive means for developing a variable signal representing mean pressure over a period of predetermined length; means responsive to output from the pressure responsive means for developing a further signal representing mean pressure over a period of given length of lesser duration than the period of predetermined duration; means responsive to the variable signal and to the further signal for developing a second control signal upon departure of the further signal from the variable signal by at least a predetermined magnitude; controllable antitachycardia pacemaking means for supplying pacing signals to the heart; means for producing controllable cardioverting/defibrillating electrical energy; control circuit means responsive to the first control signal and to the second control signal for enabling said antitachycardia pacemaking means upon presence of the first control signal and absence of the second control signal and for enabling said means for producing the cardioverting/defibrillating electrical energy upon contemporaneous presence of the first control signal and the second control signal.

47. In a system for treating a malfunctioning heart of a patient, the system including means for delivering electrical energy to the heart and pressure responsive means for sensing pressure at a site in a circulatory system, an improvement comprising means coupled to said pressure responsive means and responsive to output therefrom for producing a variable first signal representing mean pressure over a period of predetermined length; means coupled to said pressure responsive means and responsive to output therefrom for producing a second signal representing mean pressure over a period of given length of lesser duration than the period of predetermined length; means responsive to the first signal and to the second signal for producing a control signal upon occurrence of the second signal departing from the first signal by at least a given magnitude; and means responsive to the control signal for enabling the means for delivering electrical energy to the heart.

48. A system for treating a malfunctioning heart of a patient, the system comprising pressure responsive means for sensing pressure at a site in a circulatory system; means coupled to said pressure responsive means and responsive to output therefrom for producing a variable first signal representing mean pressure over a period of predetermined length; means coupled to said pressure responsive means and responsive to output therefrom for producing a second signal representing mean pressure over a period of given length of lesser duration than the period of predetermined length; means responsive to the first signal and to the second signal for producing a first control signal upon occurrence of the second signal departing from the first signal by at least a given magnitude; means responsive to heart rate for producing a second control signal upon heart rate exceeding a given rate; and means responsive to at least the first control signal and to the second control signal for delivering electrical energy to the heart.

49. In a method of treating a malfunctioning heart of a patient which includes sensing change in pressure at a site in a circulatory system and delivering to the patient electrical energy, an improvement comprising determining variable mean baseline pressure from the sensed pressure over a period of predetermined length, determining mean current pressure from the sensed pressure over a period of given length less than the duration of the predetermined period, and wherein the step of delivering electrical energy is taken in response to a difference of at least predetermined magnitude in the mean current pressure from the mean baseline pressure.

50. The method of claim 49, including determining heart rate, the step of delivering to the heart electrical energy being taken only upon the heart rate exceeding a given rate and the change of at least the predetermined magnitude in mean current pressure prevails.

51. A system for treating a malfunctioning heart, the system including storage means for storing electrical energy, electrode means for electrically coupling the storage means to the heart, pressure responsive sensing means for sensing pressure at a site in a circulatory system, means responsive to output from said sensing means for developing a variable first signal representing mean baseline pressure over a period of predetermined length, means coupled to output from said sensing means for developing a second signal representing mean current pressure over a period of given length of lesser duration than the predetermined period, means responsive to output from the means for developing the variable first signal and from the means for developing the second signal for storing the first signal upon change in mean current pressure of at least a predetermined amount from mean baseline pressure to define a stored first signal representing mean baseline pressure at time of storing, means coupled to said mean for storing the first signal and to the means for developing the second signal and responsive to the stored first signal and to the second signal for charging and enabling discharge of the electrical energy stored by said storage means across said electrode means and into the heart upon change in the mean current pressure of at least predetermined amount from the mean baseline pressure at time of storing the first signal.

52. A system for treating a malfunctioning heart, the system comprising electrical means for the sensing heart rate and producing a first control signal upon the heart rate exceeding a predetermined rate; pressure responsive sensing means for sensing pressure at a site in a circulatory system, means responsive to output from said pressure responsive sensing means for developing a first pressure-related signal representing mean baseline pressure over a period of predetermined length, means responsive to output from said pressure responsive sensing means for developing a second pressure-related signal representing mean current pressure over a period of given length of lesser duration than the period of predetermined length, means responsive to outputs from the means for developing the first pressure-related signal representing mean baseline pressure and from the means for developing the second pressure-related signal for storing the first pressure-related signal upon change in mean current pressure of at least a predetermined amount from mean baseline pressure to define a stored first pressure-related signal representing mean baseline pressure at time of storing, means coupled to said means for storing the first pressure-related signal and to the means for developing the second pressure-related signal and responsive to outputs therefrom for producing a second control signal indicative of the mean current pressure departing by at least a predetermined amount from the mean baseline pressure at the time of storing the first pressure-related signal; controllable antitachycardia pacemaking means for supplying pacing signals to the heart; controllable cardioverting/defibrillating means including storage means for storing electrical energy and electrode means for applying electrical energy from the storage means to the heart to cardiovert or to defibrillate same; control circuit means responsive to the first control signal and to the second control signal for enabling said antitachycardia pacemaking means in response to presence of the first control signal and contemporaneous absence of the second control signal and for enabling said cardioverting/defibrillating means in response to contemporaneous presence of both the first control signal and the second control signal.

53. A system for treating a malfunctioning heart, the system including means for providing cardioverting-/defibrillating electrical energy, pressure responsive sensing means for sensing pressure at a site in a circulatory system, means responsive to output from said pressure responsve sensing means for developing a variable signal representing pressure over a period of predetermined length, means responsive to output from said pressure responsive sensing means for developing a further signal representing pressure over a period of given length of lesser duration than the period of predetermined length, means responsive to the variable signal and to the further signal for storing the variable signal upon change in mean current pressure of at least a given magnitude from mean baseline pressure to define a stored signal representing mean baseline pressure at time of storing the variable signal, means coupled to said means for storing the variable signal and to the means for developing the further signal and responsive to the further signal and to the stored signal for delivering the cardioverting/defibrillating electrical energy into the heart upon occurrence of departure of the further signal from the stored signal by at least a predetermined magnitude indicative of hemodynamic comprise.

54. A system for treating a malfunctioning heart, the system comprising electrical means for sensing heart rate and producing a first control signal whenever the rate exceeds a predetermined rate; pressure responsive means for sensing pressure at a site in a circulatory system; means responsive to output from the pressure responsive means for developing a variable signal representing pressure over a period of predetermined length, means responsive to output from the pressure responsive means for developing a further signal representing pressure over a period of given length of lesser duration than the period of predetermined duration; means responsive to the variable signal and to the further signal for storing the variable signal upon change in mean current pressure of at least a given magnitude from mean baseline pressure to define a stored signal representing mean baseline pressure at time of storing the variable signal, means coupled to said means for storing the variable signal and to the means for developing the further signal and responsive to the further signal and to the stored signal for developing a second control signal upon departure of the further signal from the stored signal by at least a predetermined magnitude; controllable antitachycardia pacemaking means for supplying pacing signals to the heart; means for producing controllable cardioverting/defibrillating electrical energy; control circuit means responsive to the first control signal and to the second control signal for enabling said antitachycardia pacemaking means upon presence of the first control signal and contemporaneous absence of the second control signal and for enabling said means for producing the cardioverting/defibrillating electrical energy upon contemporaneous presence of the first control signal and the second control signal.

55. In a system for treating a malfunctioning heart of a patient, the system including means for delivering electrical energy to the heart and pressure responsive means for sensing pressure at a site in a circulatory system, an improvement comprising means coupled to said pressure responsive means and responsive to output therefrom for producing a variable first signal representing mean pressure over a period of predetermined length; means coupled to said pressure responsive means and responsive to output therefrom for producing a second signal representing the mean pressure over a period of given length of lesser duration than the period of predetermined length; means responsive to the variable first signal and to the second signal for storing the first signal upon the second signal exceeding the variable first signal by at least a predetermined amount to define a stored signal representing mean pressure over a period of the predetermined length immediately preceding instant of storing; means responsive to the stored signal and to the second signal for producing a control signal upon the second signal departing from the stored signal by at least a given magnitude; and means responsive to the control signal for enabling the means for delivering electrical energy to the heart.

56. A system for treating a malfunctioning heart of a patient, the system comprising pressure responsive means for sensing pressure at a site in a circulatory system; means coupled to said pressure responsive means and responsive to output therefrom for producing a variable first signal representing mean pressure over a period of predetermined length; means coupled to said pressure responsive means and responsive to output therefrom for producing a second signal representing mean pressure over a period of given length of lesser duration than the period of substantially predetermined length; means responsive to the variable first signal and to the second signal for storing the first signal upon the second signal exceeding the variable first signal by at least a predetermined amount to define a stored signal representing mean pressure over a period of the predetermined length immediately preceding instant of storing; means responsive to the stored signal and to the second signal for producing a first control signal upon occurence of the second signal departing from the stored signal by at least a given magnitude; means responsive to heart rate for producing a second control signal; and means responsive to the first control signal and to the second control signal for delivering electrical energy to the heart.

* * * * *